US012357494B2

(12) United States Patent
Fearn et al.

(10) Patent No.: US 12,357,494 B2
(45) Date of Patent: Jul. 15, 2025

(54) OSTOMY SYSTEMS AND METHODS

(71) Applicant: ConvaTec Technologies Inc., Las Vegas, NV (US)

(72) Inventors: Robert Fearn, Irvine, CA (US); Asif Shakeel, Irvine, CA (US); David Ramirez-Ayala, Baldwin Park, CA (US); Sabrina Kaefer, Irvine, CA (US); Irina Dorofeeva, Riverside, CA (US); Naresh C. Bhavaraju, Los Angeles, CA (US); Jeanneane Waddell, Irvine, CA (US); Thomas Yuschak, Irvine, CA (US)

(73) Assignee: CONVATEC TECHNOLOGIES INC., Las Vegas, NV (US)

( * ) Notice: Subject to any disclaimer, the term of this patent is extended or adjusted under 35 U.S.C. 154(b) by 870 days.

(21) Appl. No.: 17/450,960

(22) Filed: Oct. 14, 2021

(65) Prior Publication Data
US 2022/0117771 A1    Apr. 21, 2022

Related U.S. Application Data

(60) Provisional application No. 63/092,437, filed on Oct. 15, 2020.

(51) Int. Cl.
*A61F 5/44* (2006.01)
*A61B 5/00* (2006.01)
(Continued)

(52) U.S. Cl.
CPC ............ *A61F 5/4404* (2013.01); *A61B 5/015* (2013.01); *A61B 5/6811* (2013.01); *A61F 5/449* (2013.01); *A61B 2562/0219* (2013.01)

(58) Field of Classification Search
CPC ...... A61F 5/4404; A61B 5/015; A61B 5/6811
See application file for complete search history.

(56) References Cited

U.S. PATENT DOCUMENTS

| | | | |
|---|---|---|---|
| 28,341 A | 5/1860 | Bennett | |
| 2,875,451 A | 3/1959 | Stegeman et al. | |

(Continued)

FOREIGN PATENT DOCUMENTS

| | | |
|---|---|---|
| EP | 0064044 B1 | 2/1986 |
| EP | 0868892 A1 | 10/1998 |

(Continued)

OTHER PUBLICATIONS

Appadvice.com, Legacy Flex Alerts, last updated Oct. 26, 2018, retrieved on Dec. 30, 2019, https://appadvice.com/app/legacy-flex-alert/869412041, in 2 pages.

(Continued)

*Primary Examiner* — Daniel L Cerioni
(74) *Attorney, Agent, or Firm* — TAFT STETTINIUS HOLLISTER LLP; Ryan O. White; Derek B. Lavender

(57) ABSTRACT

A maintenance bag of an ostomy system can include fewer sensors than a diagnostic or analytic ostomy bag that is typically used for newer users. The maintenance bag can include sensors and electronics to detect fill level of the bag. The maintenance bag can also include a bag sealing mechanism that can detect drainage events and aid the user to track inventory of the bags. A wafer that can be used with an ostomy bag can include leak sensors configured to detect leak of effluent. The wafer can also include temperature sensors configured to detect inflammation. The wafer can further include a convex interface for better fit with certain users.

7 Claims, 21 Drawing Sheets

(51) Int. Cl.
    *A61B 5/01* (2006.01)
    *A61F 5/449* (2006.01)

(56) References Cited

U.S. PATENT DOCUMENTS

| | | |
|---|---|---|
| 3,507,282 A | 4/1970 | Burding |
| 3,724,461 A | 4/1973 | Eisenberg et al. |
| 3,825,005 A | 7/1974 | Fenton |
| 3,952,726 A | 4/1976 | Hennig et al. |
| 4,211,224 A | 7/1980 | Kubach et al. |
| 4,231,369 A | 11/1980 | Sorensen et al. |
| 4,338,937 A | 7/1982 | Lerman |
| 4,351,322 A | 9/1982 | Prager |
| 4,367,732 A | 1/1983 | Poulsen et al. |
| 4,382,441 A | 5/1983 | Svedman |
| 4,403,991 A | 9/1983 | Hill |
| 4,411,659 A | 10/1983 | Jensen et al. |
| 4,451,490 A | 5/1984 | Silverman et al. |
| 4,490,145 A | 12/1984 | Campbell |
| 4,518,388 A | 5/1985 | Jensen |
| 4,596,566 A | 6/1986 | Kay |
| 4,755,177 A | 7/1988 | Hill |
| 4,834,731 A | 5/1989 | Nowak et al. |
| 5,074,851 A | 9/1991 | Olsen et al. |
| 5,051,259 A | 12/1991 | Plass et al. |
| 5,085,652 A | 2/1992 | Johnsen et al. |
| 5,125,133 A | 6/1992 | Morrison |
| 5,167,650 A | 12/1992 | Johnsen et al. |
| 5,181,905 A | 1/1993 | Flam |
| 5,250,042 A | 10/1993 | Torgalkar et al. |
| 5,260,692 A | 11/1993 | Claren |
| 5,306,264 A | 4/1994 | Ferguson et al. |
| 5,348,546 A | 9/1994 | Norton |
| 5,369,130 A | 11/1994 | Numata |
| 5,401,264 A | 3/1995 | Leise, Jr. |
| 5,468,235 A | 11/1995 | La Gro |
| 5,618,276 A | 4/1997 | Leise, Jr. et al. |
| 5,658,267 A | 8/1997 | Colacello et al. |
| 5,690,623 A | 11/1997 | Lenz et al. |
| 5,714,225 A | 2/1998 | Hansen et al. |
| 5,722,965 A | 3/1998 | Kuczynski |
| 5,772,644 A | 6/1998 | Bark et al. |
| 5,800,415 A | 9/1998 | Olsen |
| 5,947,941 A | 9/1999 | Leis, Jr. et al. |
| 6,025,725 A | 2/2000 | Gershenfeld et al. |
| 6,032,831 A | 3/2000 | Gardner et al. |
| 6,135,986 A | 10/2000 | Leisner |
| 6,165,159 A | 12/2000 | Blanton |
| 6,171,289 B1 | 1/2001 | Millot et al. |
| 6,171,594 B1 | 1/2001 | Nielsen et al. |
| 6,303,700 B1 | 10/2001 | Chen |
| 6,332,879 B1 | 12/2001 | Nielsen et al. |
| 6,437,038 B1 | 8/2002 | Chen |
| 6,451,883 B1 | 9/2002 | Chen et al. |
| 6,544,241 B2 | 4/2003 | Morton |
| 6,689,111 B2 | 2/2004 | Mulhauser et al. |
| 6,709,421 B1 | 3/2004 | Falconer |
| 6,878,130 B2 | 4/2005 | Fournie et al. |
| 6,927,316 B1 | 8/2005 | Faries, Jr. et al. |
| 6,963,772 B2 | 11/2005 | Bloom et al. |
| 6,984,993 B2 | 1/2006 | Ariav |
| 7,087,041 B2 | 8/2006 | Von Dyck et al. |
| 7,094,220 B2 | 8/2006 | Tanghoj et al. |
| 7,422,577 B2 | 9/2008 | Udayakumar et al. |
| D597,606 S | 8/2009 | Chin et al. |
| 7,604,622 B2 | 10/2009 | Pedersen et al. |
| 7,727,205 B2 | 6/2010 | Leisner |
| 7,734,411 B2 | 6/2010 | Shelley et al. |
| 7,765,007 B2 | 7/2010 | Martino et al. |
| 7,947,003 B2 | 5/2011 | Bonnefin et al. |
| 8,011,505 B2 | 9/2011 | Murray et al. |
| 8,066,693 B2 | 11/2011 | Tanghoj et al. |
| 8,207,393 B2 | 6/2012 | Bach |
| 8,230,993 B2 | 7/2012 | Tanghoej |
| D665,421 S | 8/2012 | Morrow et al. |
| 8,303,554 B2 | 11/2012 | Tsai et al. |
| 8,377,019 B2 | 2/2013 | Schertiger |
| 8,382,732 B2 | 2/2013 | Oberholtzer et al. |
| 8,398,602 B2 | 3/2013 | Ilo et al. |
| 8,398,615 B2 | 3/2013 | Torstensen et al. |
| 8,409,171 B2 | 4/2013 | Hannon et al. |
| 8,460,259 B2 | 6/2013 | Tsai |
| 8,500,707 B2 | 8/2013 | Murray |
| 8,603,189 B2 | 12/2013 | Behan et al. |
| 8,636,645 B2 | 1/2014 | Daniel |
| 8,636,679 B2 | 1/2014 | Linnane et al. |
| 8,637,072 B2 | 1/2014 | Kershaw et al. |
| 8,679,581 B2 | 3/2014 | Sambasivam et al. |
| 8,684,983 B2 | 4/2014 | Andersen et al. |
| 8,740,865 B2 | 6/2014 | Krystek et al. |
| 8,808,175 B2 | 8/2014 | Deitch et al. |
| 8,845,606 B2 | 9/2014 | Nguyen-Demary et al. |
| 8,939,952 B2 | 1/2015 | Weig |
| 8,998,862 B2 | 4/2015 | Hanuka et al. |
| D731,512 S | 6/2015 | Xu |
| D733,175 S | 6/2015 | Bae |
| 9,050,387 B2 | 6/2015 | Chang et al. |
| 9,072,862 B2 | 7/2015 | Murray et al. |
| 9,095,407 B2 | 8/2015 | Deegan et al. |
| 9,216,104 B2 | 12/2015 | Thirstrup et al. |
| 9,241,824 B2 | 1/2016 | Ellering |
| 9,248,214 B2 | 2/2016 | Lykke et al. |
| 9,259,512 B2 | 2/2016 | Udayakumar et al. |
| 9,296,835 B2 | 3/2016 | Madsen et al. |
| 9,342,485 B2 | 5/2016 | Tart et al. |
| 9,353,211 B2 | 5/2016 | Madsen et al. |
| D758,443 S | 6/2016 | Kang |
| 9,399,633 B2 | 7/2016 | Madsen et al. |
| 9,427,548 B2 | 8/2016 | Triel |
| D769,921 S | 10/2016 | Smith |
| D771,660 S | 11/2016 | Zimmerman et al. |
| D774,061 S | 12/2016 | Wu |
| 9,526,816 B2 | 12/2016 | Toth |
| D777,733 S | 1/2017 | Loosli et al. |
| 9,549,839 B2 | 1/2017 | Schertiger et al. |
| 9,562,305 B2 | 2/2017 | Bonnefin et al. |
| D781,299 S | 3/2017 | Yun et al. |
| 9,585,784 B2 | 3/2017 | Matthiassen et al. |
| 9,636,286 B2 | 5/2017 | Grundhofer |
| 9,642,737 B2 | 5/2017 | Seres et al. |
| 9,649,230 B1 | 5/2017 | Li |
| 9,687,313 B2 | 6/2017 | Todd et al. |
| 9,717,490 B2 | 8/2017 | Deitch |
| D797,797 S | 9/2017 | Gandhi et al. |
| 9,763,833 B2 | 9/2017 | Taylor et al. |
| 9,770,548 B2 | 9/2017 | Gilman |
| 9,795,484 B2 | 10/2017 | Daniel |
| 9,801,754 B2 | 10/2017 | Masters et al. |
| D803,258 S | 11/2017 | Graham et al. |
| D804,522 S | 12/2017 | Sachtleben et al. |
| 9,848,866 B2 | 12/2017 | Daniel |
| 9,861,781 B2 | 1/2018 | Murray et al. |
| 9,877,818 B2 | 1/2018 | Poucher et al. |
| D810,770 S | 2/2018 | Trahan et al. |
| D819,067 S | 5/2018 | Behzadi et al. |
| D819,068 S | 5/2018 | Scheel et al. |
| 9,956,079 B2 | 5/2018 | Daniel |
| 9,962,282 B2 | 5/2018 | Chang et al. |
| 9,968,480 B2 | 5/2018 | Nyberg |
| 9,974,682 B2 | 5/2018 | Schertiger et al. |
| 9,999,537 B2 | 6/2018 | Ekfeldt et al. |
| 10,045,877 B2 | 8/2018 | Weig |
| 10,045,878 B2 | 8/2018 | Freiding |
| 10,058,638 B2 | 8/2018 | Gravesen et al. |
| D829,225 S | 9/2018 | Gandhi et al. |
| 10,065,014 B2 | 9/2018 | Hagel |
| 10,071,012 B2 | 9/2018 | Larson et al. |
| 10,076,394 B2 | 9/2018 | Browning |
| 10,076,438 B2 | 9/2018 | Bendix et al. |
| 10,076,636 B2 | 9/2018 | Murray et al. |
| 10,076,660 B2 | 9/2018 | Gyrn |
| 10,092,250 B2 | 10/2018 | Tucker et al. |
| 10,092,441 B2 | 10/2018 | Lee |
| 10,105,255 B2 | 10/2018 | Fattman et al. |

(56) References Cited

U.S. PATENT DOCUMENTS

| | | |
|---|---|---|
| 10,117,783 B2 | 11/2018 | Cotton et al. |
| 10,118,018 B2 | 11/2018 | Foley et al. |
| 10,118,019 B2 | 11/2018 | Murray et al. |
| 10,123,908 B2 | 11/2018 | Everland et al. |
| 10,136,981 B2 | 11/2018 | Poucher et al. |
| 10,166,136 B2 | 1/2019 | Poucher |
| 10,166,137 B2 | 1/2019 | Nguyen-Demary et al. |
| 10,166,138 B2 | 1/2019 | Cline et al. |
| 10,166,366 B2 | 1/2019 | Murray et al. |
| 10,179,823 B2 | 1/2019 | Kershaw et al. |
| 10,182,914 B2 | 1/2019 | Daniel |
| 10,183,112 B2 | 1/2019 | Foley et al. |
| D841,660 S | 2/2019 | Mercado |
| 10,194,938 B2 | 2/2019 | Byager |
| 10,195,066 B2 | 2/2019 | Behan |
| 10,195,069 B2 | 2/2019 | Jepsen et al. |
| 10,195,075 B2 | 2/2019 | Scott et al. |
| 10,207,031 B2 | 2/2019 | Toth |
| 10,207,076 B2 | 2/2019 | Foley et al. |
| D843,404 S | 3/2019 | Spector |
| 10,219,953 B2 | 3/2019 | Dewitt et al. |
| 10,220,185 B2 | 3/2019 | Sadik et al. |
| 10,226,317 B2 | 3/2019 | Deitch et al. |
| 10,226,318 B2 | 3/2019 | McClurg |
| 10,231,876 B2 | 3/2019 | Igwebuike et al. |
| 10,238,526 B2 | 3/2019 | Daniel et al. |
| 10,251,770 B2 | 4/2019 | Chang et al. |
| 10,251,773 B2 | 4/2019 | Schertiger et al. |
| 10,251,973 B2 | 4/2019 | Lam et al. |
| 10,252,291 B2 | 4/2019 | Madsen et al. |
| 10,278,691 B2 | 5/2019 | McClurg et al. |
| 10,278,800 B2 | 5/2019 | Suslian et al. |
| 10,278,822 B2 | 5/2019 | Daniel |
| 10,278,857 B2 | 5/2019 | Hansen et al. |
| 10,285,847 B2 | 5/2019 | Lesko et al. |
| 10,294,317 B2 | 5/2019 | Sambasivam et al. |
| 10,299,956 B2 | 5/2019 | Schertiger et al. |
| 10,321,983 B2 | 6/2019 | Sobrino-Serrano et al. |
| 10,322,024 B2 | 6/2019 | Chang |
| 10,322,026 B2 | 6/2019 | Hansen et al. |
| 10,335,185 B2 | 7/2019 | Uihlein |
| 10,335,309 B2 | 7/2019 | Becker et al. |
| 10,342,890 B2 | 7/2019 | Bray |
| 10,363,027 B2 | 7/2019 | Dravis et al. |
| 10,369,268 B2 | 8/2019 | Frostaa et al. |
| 10,376,637 B2 | 8/2019 | Gyrn et al. |
| 10,383,730 B2 | 8/2019 | Daniel |
| 10,391,197 B2 | 8/2019 | Woods |
| D860,222 S | 9/2019 | Cen |
| 10,398,429 B2 | 9/2019 | Poucher et al. |
| 10,398,558 B2 | 9/2019 | Crabb |
| 10,406,277 B2 | 9/2019 | Gregory |
| 10,406,322 B2 | 9/2019 | O'Flynn et al. |
| 10,420,859 B2 | 9/2019 | Rostami et al. |
| 10,426,584 B2 | 10/2019 | McClurg |
| 10,426,918 B2 | 10/2019 | Foley et al. |
| 10,434,015 B2 | 10/2019 | Taylor et al. |
| 10,434,241 B2 | 10/2019 | Hvid et al. |
| 10,434,282 B2 | 10/2019 | Kearns et al. |
| 10,441,454 B2 | 10/2019 | Tanghoej et al. |
| 10,449,025 B2 | 10/2019 | Browning et al. |
| 10,449,082 B2 | 10/2019 | Johnsen |
| 10,449,328 B2 | 10/2019 | Tanghoej et al. |
| 10,449,329 B2 | 10/2019 | Foley et al. |
| 10,456,230 B2 | 10/2019 | Schuchardt et al. |
| D865,795 S | 11/2019 | Koo |
| 10,463,833 B2 | 11/2019 | Clarke et al. |
| 10,470,917 B2 | 11/2019 | Chang et al. |
| 10,470,918 B2 | 11/2019 | Bendix |
| 10,470,936 B2 | 11/2019 | Wohlgemuth et al. |
| 10,478,203 B2 | 11/2019 | Uihlein |
| 10,478,329 B2 | 11/2019 | Oberholtzer et al. |
| D869,479 S | 12/2019 | Pillalamarri et al. |
| 10,493,101 B2 | 12/2019 | Percival et al. |
| 10,493,230 B2 | 12/2019 | Guldager et al. |
| 10,493,231 B2 | 12/2019 | McMenamin et al. |
| 10,499,938 B2 | 12/2019 | Torchio et al. |
| 10,500,084 B2 | 12/2019 | Hansen et al. |
| 10,500,315 B2 | 12/2019 | Chang et al. |
| 10,507,126 B2 | 12/2019 | Matthison-Hansen et al. |
| 10,507,318 B2 | 12/2019 | Jin et al. |
| 10,512,256 B2 | 12/2019 | Kavanagh et al. |
| 10,517,754 B2 | 12/2019 | Praame et al. |
| 10,531,690 B2 | 1/2020 | Dooly et al. |
| 10,531,977 B2 | 1/2020 | Schoess et al. |
| 10,532,148 B2 | 1/2020 | Frostaa et al. |
| 10,543,133 B2 | 1/2020 | Shaw et al. |
| 10,561,817 B2 | 2/2020 | Hannon et al. |
| 10,569,047 B2 | 2/2020 | Farrell et al. |
| D879,118 S | 3/2020 | Chen et al. |
| D879,803 S | 3/2020 | Corona et al. |
| D879,804 S | 3/2020 | Corona et al. |
| 10,576,262 B2 | 3/2020 | Tsai et al. |
| 10,583,029 B2 | 3/2020 | Chang |
| 10,588,747 B2 | 3/2020 | Allen et al. |
| 10,588,773 B2 | 3/2020 | Tsai et al. |
| 10,617,504 B2 | 4/2020 | Poucher et al. |
| 10,617,789 B2 | 4/2020 | O'Mahony et al. |
| 10,631,856 B2 | 4/2020 | Hakky |
| 10,639,138 B2 | 5/2020 | Browning |
| 10,639,451 B2 | 5/2020 | Kearns et al. |
| 10,646,688 B2 | 5/2020 | Hannon et al. |
| 10,660,757 B2 | 5/2020 | Taylor |
| 10,682,213 B2 | 6/2020 | Browning |
| 10,682,233 B2 | 6/2020 | Wolf |
| 10,687,985 B2 | 6/2020 | Lee et al. |
| 10,695,229 B2 | 6/2020 | Toth |
| 10,696,626 B2 | 6/2020 | Fristrup et al. |
| D890,810 S | 7/2020 | Smith et al. |
| 10,702,632 B2 | 7/2020 | Gravesen et al. |
| 10,706,744 B2 | 7/2020 | Taylor et al. |
| 10,709,825 B2 | 7/2020 | Huang et al. |
| 10,722,366 B2 | 7/2020 | Zimmermann et al. |
| D893,514 S | 8/2020 | Stapleton |
| D894,209 S | 8/2020 | Cheng et al. |
| 10,729,546 B2 | 8/2020 | Poucher et al. |
| 10,729,806 B2 | 8/2020 | Bingol et al. |
| 10,736,769 B2 | 8/2020 | Grove Sund et al. |
| 10,737,013 B2 | 8/2020 | Foley et al. |
| 10,739,352 B2 | 8/2020 | Percival et al. |
| 10,744,224 B2 | 8/2020 | Israelson et al. |
| 10,751,442 B2 | 8/2020 | Bonnefin et al. |
| 10,751,493 B2 | 8/2020 | Gregory et al. |
| 10,758,400 B2 | 9/2020 | Cisko et al. |
| 10,758,704 B2 | 9/2020 | Hickmott et al. |
| 10,765,520 B2 | 9/2020 | Hakky |
| 10,765,796 B2 | 9/2020 | Foley et al. |
| 10,765,833 B2 | 9/2020 | Kearns |
| 10,772,755 B2 | 9/2020 | Gregory |
| 10,772,790 B2 | 9/2020 | Wild et al. |
| 10,779,993 B2 | 9/2020 | Bishop et al. |
| 10,780,199 B2 | 9/2020 | Gilman |
| 10,780,200 B2 | 9/2020 | Toth |
| 10,792,184 B2 | 10/2020 | Hvid et al. |
| 10,799,385 B2 | 10/2020 | Hansen et al. |
| 10,807,287 B2 | 10/2020 | Rolsted et al. |
| 10,813,786 B2 | 10/2020 | Lysgaard |
| D907,654 S | 1/2021 | Henegar |
| D909,404 S | 2/2021 | Bilancio et al. |
| D914,717 S | 3/2021 | Mensinger et al. |
| D918,930 S | 5/2021 | Dill et al. |
| D921,017 S | 6/2021 | Langan |
| 11,135,084 B2 | 10/2021 | Seres et al. |
| D935,477 S | 11/2021 | Champagne et al. |
| 2002/0077611 A1 | 6/2002 | Vonk Dyck et al. |
| 2003/0181879 A1 | 9/2003 | Mulhauser et al. |
| 2003/0199783 A1 | 10/2003 | Bloom et al. |
| 2003/0236509 A1 | 12/2003 | Silvestrini |
| 2004/0049837 A1 | 3/2004 | Falconer et al. |
| 2004/0073151 A1 | 4/2004 | Weston |
| 2005/0065485 A1 | 3/2005 | Andersen et al. |
| 2005/0131360 A1 | 6/2005 | Villefrance et al. |
| 2005/0143696 A1 | 6/2005 | Pedersen et al. |

(56) References Cited

U.S. PATENT DOCUMENTS

| | | | |
|---|---|---|---|
| 2008/0107225 A1* | 5/2008 | Hashemian | G07C 3/08 |
| | | | 376/247 |
| 2008/0275327 A1 | 11/2008 | Faarbaek et al. | |
| 2008/0288026 A1 | 11/2008 | Cross et al. | |
| 2009/0157140 A1 | 6/2009 | Martino | |
| 2010/0010460 A1 | 1/2010 | Butler | |
| 2010/0030167 A1 | 2/2010 | Thirstrup et al. | |
| 2010/0145291 A1 | 6/2010 | Kambara | |
| 2010/0174253 A1 | 7/2010 | Cline et al. | |
| 2011/0028924 A1 | 2/2011 | Murray | |
| 2011/0040270 A1 | 2/2011 | Ciok et al. | |
| 2011/0060362 A1 | 3/2011 | Patel et al. | |
| 2011/0092929 A1 | 4/2011 | Weig | |
| 2011/0224653 A1 | 9/2011 | Torstensen et al. | |
| 2012/0116447 A1 | 5/2012 | Stanley et al. | |
| 2012/0136324 A1 | 5/2012 | Hanuka et al. | |
| 2012/0245519 A1 | 9/2012 | Rotella et al. | |
| 2013/0053802 A1 | 2/2013 | Maidl et al. | |
| 2013/0132854 A1 | 5/2013 | Raleigh et al. | |
| 2013/0226117 A1 | 8/2013 | Hansen et al. | |
| 2013/0274696 A1 | 10/2013 | Lam | |
| 2013/0324952 A1 | 12/2013 | Krystek et al. | |
| 2014/0039429 A1 | 2/2014 | Stroebech et al. | |
| 2014/0128826 A1 | 5/2014 | Klein et al. | |
| 2014/0194843 A1 | 7/2014 | Masters et al. | |
| 2015/0051587 A1 | 2/2015 | Rolsted et al. | |
| 2015/0164679 A1 | 6/2015 | Maidl et al. | |
| 2015/0188720 A1 | 7/2015 | Winter | |
| 2015/0250639 A1 | 9/2015 | Thirstrup et al. | |
| 2015/0297861 A1 | 10/2015 | Passalaqua et al. | |
| 2015/0306342 A1 | 10/2015 | Rostami et al. | |
| 2015/0351690 A1 | 12/2015 | Toth et al. | |
| 2016/0113810 A1 | 4/2016 | Hanuka et al. | |
| 2016/0158056 A1 | 6/2016 | Davis et al. | |
| 2016/0171011 A1 | 6/2016 | Drogobetski et al. | |
| 2016/0220743 A1 | 8/2016 | Guthrie et al. | |
| 2016/0310642 A1 | 10/2016 | Clarke et al. | |
| 2017/0000642 A1 | 1/2017 | Cisko et al. | |
| 2017/0079576 A1 | 3/2017 | Stroebech et al. | |
| 2017/0105657 A1 | 4/2017 | Eid | |
| 2017/0140103 A1 | 5/2017 | Angelides | |
| 2017/0201850 A1 | 7/2017 | Raleigh et al. | |
| 2017/0224523 A1 | 8/2017 | Bendix | |
| 2017/0239384 A1 | 8/2017 | Lam et al. | |
| 2017/0340804 A1 | 11/2017 | Hvid et al. | |
| 2017/0348137 A1 | 12/2017 | Hvid et al. | |
| 2018/0008451 A1 | 1/2018 | Stroebech | |
| 2018/0021474 A1 | 1/2018 | Stroebech et al. | |
| 2018/0043086 A1 | 2/2018 | Foley et al. | |
| 2018/0104089 A1 | 4/2018 | Nyberg et al. | |
| 2018/0116859 A1 | 5/2018 | Strobech et al. | |
| 2018/0133359 A1 | 5/2018 | Hossain et al. | |
| 2018/0133360 A1 | 5/2018 | Bingol et al. | |
| 2018/0147093 A1 | 5/2018 | Igwebuike et al. | |
| 2018/0169377 A1 | 6/2018 | Hickmott et al. | |
| 2018/0177626 A1 | 6/2018 | Israelson | |
| 2018/0229013 A1 | 8/2018 | Tsai | |
| 2018/0235802 A1 | 8/2018 | Nguyen-Demary et al. | |
| 2018/0243466 A1 | 8/2018 | Israelson et al. | |
| 2018/0250120 A1 | 9/2018 | Behan | |
| 2018/0250156 A1 | 9/2018 | Lam | |
| 2018/0250157 A1 | 9/2018 | Masters et al. | |
| 2018/0250170 A1 | 9/2018 | Oelund et al. | |
| 2018/0256020 A1 | 9/2018 | Taylor et al. | |
| 2018/0256402 A1 | 9/2018 | Janis | |
| 2018/0263804 A1 | 9/2018 | Stroebech et al. | |
| 2018/0263805 A1 | 9/2018 | Lam et al. | |
| 2018/0272105 A1 | 9/2018 | Triel et al. | |
| 2018/0280659 A1 | 10/2018 | Kearns et al. | |
| 2018/0289527 A1 | 10/2018 | Vila | |
| 2018/0289852 A1 | 10/2018 | Woods | |
| 2018/0311066 A1 | 11/2018 | Hansen et al. | |
| 2018/0311420 A1 | 11/2018 | Cotton | |
| 2018/0318125 A1 | 11/2018 | Casado et al. | |
| 2018/0318126 A1 | 11/2018 | Weig | |
| 2018/0318127 A1 | 11/2018 | Nielsen et al. |
| 2018/0325718 A1 | 11/2018 | Ekfeldt et al. |
| 2018/0333290 A1 | 11/2018 | Jones et al. |
| 2018/0333518 A1 | 11/2018 | Gravesen et al. |
| 2018/0338849 A1 | 11/2018 | Behan |
| 2018/0353317 A1 | 12/2018 | Bendix et al. |
| 2018/0360645 A1 | 12/2018 | Fattman et al. |
| 2018/0362690 A1 | 12/2018 | Sambasivam et al. |
| 2018/0369010 A1 | 12/2018 | Lee |
| 2018/0369474 A1 | 12/2018 | Falleboe et al. |
| 2019/0000324 A1 | 1/2019 | Laugaard Nielsen |
| 2019/0000627 A1 | 1/2019 | Wolf |
| 2019/0015186 A1 | 1/2019 | Poucher et al. |
| 2019/0015242 A1 | 1/2019 | Oeelund |
| 2019/0021912 A1 | 1/2019 | Cotton et al. |
| 2019/0029868 A1 | 1/2019 | Grum-Schwensen et al. |
| 2019/0030214 A1 | 1/2019 | Montes de Oca et al. |
| 2019/0046718 A1 | 2/2019 | Henry et al. |
| 2019/0070034 A1 | 3/2019 | Udayakumar |
| 2019/0083295 A1 | 3/2019 | Cisko et al. |
| 2019/0083746 A1 | 3/2019 | Murray et al. |
| 2019/0099284 A1 | 4/2019 | Augustyn et al. |
| 2019/0105462 A1 | 4/2019 | Schertiger |
| 2019/0117441 A1 | 4/2019 | Hansen et al. |
| 2019/0117824 A1 | 4/2019 | Hansen et al. |
| 2019/0117876 A1 | 4/2019 | Foley et al. |
| 2019/0125570 A1 | 5/2019 | Jones et al. |
| 2019/0126004 A1 | 5/2019 | O'Brien et al. |
| 2019/0133810 A1 | 5/2019 | Seres et al. |
| 2019/0133811 A1 | 5/2019 | Seres et al. |
| 2019/0133812 A1 | 5/2019 | Seres et al. |
| 2019/0133813 A1 | 5/2019 | Cline et al. |
| 2019/0133830 A1 | 5/2019 | Bishop et al. |
| 2019/0134256 A1 | 5/2019 | Stroebech |
| 2019/0134280 A1 | 5/2019 | Toth |
| 2019/0142623 A1 | 5/2019 | Schoess |
| 2019/0142642 A1 | 5/2019 | Burnet et al. |
| 2019/0151063 A1 | 5/2019 | Deitch et al. |
| 2019/0151134 A1 | 5/2019 | Tsai et al. |
| 2019/0151158 A1 | 5/2019 | Dewitt et al. |
| 2019/0151515 A1 | 5/2019 | Selby et al. |
| 2019/0151605 A1 | 5/2019 | McMenamin et al. |
| 2019/0151610 A1 | 5/2019 | Fletter |
| 2019/0153168 A1 | 5/2019 | Behan et al. |
| 2019/0159940 A1 | 5/2019 | Selby et al. |
| 2019/0167303 A1 | 6/2019 | Byager |
| 2019/0167485 A9 | 6/2019 | Oelund et al. |
| 2019/0192066 A1 | 6/2019 | Schoess et al. |
| 2019/0192333 A1 | 6/2019 | Hansen et al. |
| 2019/0192334 A1 | 6/2019 | Hansen et al. |
| 2019/0201236 A1 | 7/2019 | Scott et al. |
| 2019/0201589 A1 | 7/2019 | Farrell et al. |
| 2019/0224402 A1 | 7/2019 | Henry et al. |
| 2019/0231581 A1 | 8/2019 | Chang |
| 2019/0247220 A1 | 8/2019 | Lesko et al. |
| 2019/0247549 A1 | 8/2019 | Nielsen |
| 2019/0254864 A1 | 8/2019 | Czaplewski et al. |
| 2019/0262026 A1 | 8/2019 | Uihlein |
| 2019/0262166 A1 | 8/2019 | Becker et al. |
| 2019/0266129 A1 | 8/2019 | Huang et al. |
| 2019/0274672 A1 | 9/2019 | Allen |
| 2019/0287424 A1 | 9/2019 | Taylor et al. |
| 2019/0290220 A9 | 9/2019 | Tucker et al. |
| 2019/0290472 A1 | 9/2019 | Schertiger et al. |
| 2019/0290806 A1 | 9/2019 | Farrell et al. |
| 2019/0298895 A1 | 10/2019 | Selby et al. |
| 2019/0307904 A1 | 10/2019 | Ballamy |
| 2019/0308935 A1 | 10/2019 | Fristrup et al. |
| 2019/0321587 A1 | 10/2019 | McMenamin et al. |
| 2019/0328380 A1 | 10/2019 | Poucher et al. |
| 2019/0328572 A1 | 10/2019 | Weinberg et al. |
| 2019/0343617 A1 | 11/2019 | Sobrino-Serrano et al. |
| 2019/0358015 A1 | 11/2019 | Deitch et al. |
| 2019/0358016 A1 | 11/2019 | Deitch et al. |
| 2019/0374163 A1 | 12/2019 | Faarbaek et al. |
| 2019/0380882 A1 | 12/2019 | Taylor et al. |
| 2019/0381273 A1 | 12/2019 | Kearns et al. |
| 2019/0381276 A1 | 12/2019 | Foley et al. |
| 2019/0388226 A1 | 12/2019 | Crabb et al. |

(56) References Cited

U.S. PATENT DOCUMENTS

| | | |
|---|---|---|
| 2020/0001043 A1 | 1/2020 | Heneghan et al. |
| 2020/0015996 A1 | 1/2020 | Schertiger |
| 2020/0016366 A1 | 1/2020 | Murray et al. |
| 2020/0016380 A1 | 1/2020 | Murray et al. |
| 2020/0030152 A1 | 1/2020 | Wohlgemuth et al. |
| 2020/0030497 A1 | 1/2020 | Chang et al. |
| 2020/0030521 A1 | 1/2020 | Gregory |
| 2020/0038226 A1 | 2/2020 | Botten et al. |
| 2020/0038529 A1 | 2/2020 | Farrell et al. |
| 2020/0038535 A1 | 2/2020 | Montes De Oca et al. |
| 2020/0046540 A1 | 2/2020 | Cisko et al. |
| 2020/0046541 A1 | 2/2020 | Sund et al. |
| 2020/0046543 A1 | 2/2020 | Scalise et al. |
| 2020/0054795 A1 | 2/2020 | Farrell et al. |
| 2020/0060863 A1 | 2/2020 | Sund et al. |
| 2020/0061282 A1 | 2/2020 | Hvid et al. |
| 2020/0061335 A1 | 2/2020 | Guldager |
| 2020/0069455 A1 | 3/2020 | Oberholtzer et al. |
| 2020/0078030 A1 | 3/2020 | Torchio et al. |
| 2020/0078510 A1 | 3/2020 | Henry et al. |
| 2020/0093632 A1 | 3/2020 | Kavanagh et al. |
| 2020/0100931 A1 | 4/2020 | Schoess et al. |
| 2020/0100946 A1 | 4/2020 | Wohlgemuth et al. |
| 2020/0109106 A1 | 4/2020 | Vange et al. |
| 2020/0138619 A1 | 5/2020 | Cisko et al. |
| 2020/0146827 A1 | 5/2020 | Allen et al. |
| 2020/0147273 A1 | 5/2020 | O'Mahony et al. |
| 2020/0155261 A1 | 5/2020 | O'Flynn et al. |
| 2020/0155319 A1 | 5/2020 | Allen et al. |
| 2020/0155320 A1 | 5/2020 | Allen et al. |
| 2020/0155379 A1 | 5/2020 | Shaw et al. |
| 2020/0155796 A1 | 5/2020 | Hannon et al. |
| 2020/0163792 A1 | 5/2020 | Schertiger |
| 2020/0163793 A1 | 5/2020 | Chang |
| 2020/0164196 A1 | 5/2020 | Jin et al. |
| 2020/0170829 A1 | 6/2020 | Tsai et al. |
| 2020/0178988 A1 | 6/2020 | Henry et al. |
| 2020/0179590 A1 | 6/2020 | Henry et al. |
| 2020/0179644 A1 | 6/2020 | Guldbaek |
| 2020/0188160 A1 | 6/2020 | Udayakumar |
| 2020/0188161 A1* | 6/2020 | Seres ................ G01K 13/00 |
| 2020/0188631 A1 | 6/2020 | Hannon et al. |
| 2020/0197145 A1 | 6/2020 | Morningstar et al. |
| 2020/0206389 A1 | 7/2020 | Vange |
| 2020/0206411 A1 | 7/2020 | Henry et al. |
| 2020/0214896 A1 | 7/2020 | Igwebuike et al. |
| 2020/0215256 A1 | 7/2020 | Henry et al. |
| 2020/0222587 A1 | 7/2020 | O'Mahony et al. |
| 2020/0222651 A1 | 7/2020 | Jockel et al. |
| 2020/0222659 A1 | 7/2020 | Schertiger et al. |
| 2020/0229962 A1 | 7/2020 | Torstensen et al. |
| 2020/0230349 A1 | 7/2020 | McMenamin et al. |
| 2020/0231715 A1 | 7/2020 | Hoj et al. |
| 2020/0246173 A1 | 8/2020 | Schertiger et al. |
| 2020/0246174 A1 | 8/2020 | Hansen et al. |
| 2020/0246175 A1 | 8/2020 | Hansen et al. |
| 2020/0246176 A1 | 8/2020 | Hansen et al. |
| 2020/0246177 A1 | 8/2020 | Hansen et al. |
| 2020/0253777 A1 | 8/2020 | Jones |
| 2020/0254156 A1 | 8/2020 | Toth |
| 2020/0282177 A1 | 9/2020 | Farrell |
| 2020/0289269 A1 | 9/2020 | Hakky |
| 2020/0289326 A1 | 9/2020 | Nielsen et al. |
| 2020/0289327 A1 | 9/2020 | Hansen et al. |
| 2020/0289346 A1 | 9/2020 | Taylor et al. |
| 2020/0294425 A1 | 9/2020 | Taylor et al. |
| 2020/0299865 A1 | 9/2020 | Bonnefin et al. |
| 2020/0306045 A1 | 10/2020 | Crabb |
| 2020/0306073 A1 | 10/2020 | Olsen et al. |
| 2020/0306074 A1 | 10/2020 | Speiermann et al. |
| 2020/0306091 A1 | 10/2020 | Lee et al. |
| 2020/0316287 A1 | 10/2020 | Foley et al. |
| 2020/0324019 A1 | 10/2020 | Calo et al. |
| 2020/0330258 A1 | 10/2020 | Hansen et al. |
| 2020/0330259 A1 | 10/2020 | Sund et al. |
| 2020/0330260 A1 | 10/2020 | Hansen et al. |
| 2020/0337879 A1 | 10/2020 | Donovan et al. |
| 2020/0337880 A1 | 10/2020 | Hansen et al. |
| 2020/0337881 A1 | 10/2020 | Hansen et al. |
| 2020/0337882 A1 | 10/2020 | Hansen et al. |
| 2020/0337883 A1 | 10/2020 | Hansen et al. |
| 2020/0337884 A1 | 10/2020 | Donovan et al. |
| 2020/0337885 A1 | 10/2020 | Donovan et al. |
| 2020/0338230 A1 | 10/2020 | Israelson et al. |
| 2020/0345498 A1 | 11/2020 | Poucher et al. |
| 2020/0345903 A1 | 11/2020 | Selby et al. |
| 2020/0345977 A1 | 11/2020 | Hickmott et al. |
| 2020/0383821 A1* | 12/2020 | Hansen ................ A61F 5/44 |
| 2023/0240882 A1 | 8/2023 | Seres et al. |

FOREIGN PATENT DOCUMENTS

| | | |
|---|---|---|
| EP | 1188157 B1 | 12/2005 |
| EP | 2407112 B1 | 1/2012 |
| EP | 2407129 B1 | 1/2013 |
| EP | 1629860 B2 | 8/2017 |
| EP | 2950761 B1 | 8/2017 |
| EP | 1610715 B1 | 11/2018 |
| EP | 3100702 B1 | 12/2018 |
| EP | 3427673 A1 | 1/2019 |
| EP | 2787939 B1 | 3/2019 |
| EP | 3226775 B1 | 3/2019 |
| EP | 2977074 B1 | 5/2019 |
| EP | 3292839 B1 | 5/2019 |
| EP | 2977075 B1 | 6/2019 |
| EP | 3028673 B1 | 7/2019 |
| EP | 3001983 B1 | 8/2019 |
| EP | 2480169 B1 | 11/2019 |
| EP | 3001976 B1 | 11/2019 |
| EP | 3001980 B1 | 11/2019 |
| EP | 3563807 A1 | 11/2019 |
| EP | 3574870 A1 | 12/2019 |
| EP | 3351208 B1 | 1/2020 |
| EP | 3116559 B1 | 2/2020 |
| EP | 3001981 B1 | 3/2020 |
| EP | 3092025 B1 | 3/2020 |
| EP | 3620198 A1 | 3/2020 |
| EP | 1649839 B1 | 4/2020 |
| EP | 2157944 B1 | 4/2020 |
| EP | 2337538 B1 | 4/2020 |
| EP | 3115024 B1 | 4/2020 |
| EP | 3446738 B1 | 4/2020 |
| EP | 3636290 A1 | 4/2020 |
| EP | 2091567 B1 | 5/2020 |
| EP | 2121062 B1 | 5/2020 |
| EP | 2804534 B1 | 5/2020 |
| EP | 2804537 B1 | 5/2020 |
| EP | 2968834 B1 | 5/2020 |
| EP | 3079748 B1 | 5/2020 |
| EP | 3079750 B1 | 5/2020 |
| EP | 3160732 B1 | 5/2020 |
| EP | 3175829 B1 | 5/2020 |
| EP | 3346961 B1 | 5/2020 |
| EP | 3481460 B1 | 5/2020 |
| EP | 3653236 A1 | 5/2020 |
| EP | 2651485 B1 | 6/2020 |
| EP | 2908998 B1 | 6/2020 |
| EP | 2916901 B1 | 6/2020 |
| EP | 3175830 B1 | 6/2020 |
| EP | 3470025 B1 | 6/2020 |
| EP | 3662873 A1 | 6/2020 |
| EP | 3666321 A1 | 6/2020 |
| EP | 2854722 B1 | 7/2020 |
| EP | 3232996 B1 | 7/2020 |
| EP | 3261700 B1 | 7/2020 |
| EP | 3302306 B1 | 7/2020 |
| EP | 3307370 B1 | 7/2020 |
| EP | 3389741 B1 | 7/2020 |
| EP | 3506955 B1 | 7/2020 |
| EP | 2854881 B1 | 8/2020 |
| EP | 3692956 A1 | 8/2020 |
| EP | 3698839 A1 | 8/2020 |
| EP | 3069688 B1 | 9/2020 |
| EP | 3119464 B1 | 9/2020 |

(56) References Cited

FOREIGN PATENT DOCUMENTS

| | | |
|---|---|---|
| EP | 3238671 B1 | 9/2020 |
| EP | 3278773 B1 | 9/2020 |
| EP | 3539511 B1 | 9/2020 |
| EP | 3708125 A2 | 9/2020 |
| EP | 3038670 B1 | 10/2020 |
| EP | 3170473 B1 | 10/2020 |
| EP | 3210909 B1 | 10/2020 |
| EP | 3554580 B1 | 10/2020 |
| EP | 2653132 B1 | 11/2020 |
| EP | 3733137 A1 | 11/2020 |
| EP | 3706619 B1 | 4/2024 |
| EP | 4368156 A2 | 5/2024 |
| GB | 2139501 A | 11/1984 |
| GB | 2265832 A | 10/1993 |
| GB | 2431239 A | 4/2007 |
| GB | 2510599 A | 8/2014 |
| IN | 200000444 P1 | 1/2006 |
| JP | J11319082 A | 11/1999 |
| WO | WO 90/11501 A1 | 10/1990 |
| WO | WO 1991/001118 A1 | 2/1991 |
| WO | WO 1991/001119 A1 | 2/1991 |
| WO | WO 1993/018725 A1 | 9/1993 |
| WO | WO 94/15190 A1 | 7/1994 |
| WO | WO 1994/018919 A1 | 9/1994 |
| WO | WO 1995/051173 A2 | 10/1999 |
| WO | WO 00/00232 A1 | 1/2000 |
| WO | WO 2000/007653 A1 | 2/2000 |
| WO | WO 01/13830 A1 | 3/2001 |
| WO | WO 00/000082 A1 | 8/2001 |
| WO | WO 2001/054632 A1 | 8/2001 |
| WO | WO 03/026540 A1 | 4/2003 |
| WO | WO 2003/048998 A2 | 6/2003 |
| WO | WO 2003/065946 A1 | 8/2003 |
| WO | WO 2004/004612 A1 | 1/2004 |
| WO | WO 2004/047630 A1 | 6/2004 |
| WO | WO 2005/032652 A1 | 4/2005 |
| WO | WO 2005/051316 A2 | 6/2005 |
| WO | WO 2005/099644 A2 | 10/2005 |
| WO | WO 2007/098762 A1 | 9/2007 |
| WO | WO 2010/030426 A1 | 3/2010 |
| WO | WO 2010/060115 A1 | 5/2010 |
| WO | WO 2010/106039 A1 | 9/2010 |
| WO | WO 2012/059906 A1 | 5/2012 |
| WO | WO 2013/022575 A1 | 2/2013 |
| WO | WO 2014/102537 A1 | 7/2014 |
| WO | WO 2015/148035 A1 | 10/2015 |
| WO | WO 2017/136314 A1 | 8/2017 |
| WO | WO 2017/152921 A1 | 9/2017 |
| WO | WO 2017/168249 A2 | 10/2017 |
| WO | WO 2017/192685 A1 | 11/2017 |
| WO | WO 2017/222780 A1 | 12/2017 |
| WO | WO 2018/009818 A1 | 1/2018 |
| WO | WO 2018/009880 A1 | 1/2018 |
| WO | WO 2018/028756 A1 | 2/2018 |
| WO | WO 2018/071804 A2 | 4/2018 |
| WO | WO 2018/111713 A1 | 6/2018 |
| WO | WO 2018/149463 A2 | 8/2018 |
| WO | WO 2018/156502 A2 | 8/2018 |
| WO | WO 2018/156589 A2 | 8/2018 |
| WO | WO 2018/177488 A1 | 10/2018 |
| WO | WO 2018/183128 A1 | 10/2018 |
| WO | WO 2018/187427 A1 | 10/2018 |
| WO | WO 2018/188706 A1 | 10/2018 |
| WO | WO 2018/188707 A1 | 10/2018 |
| WO | WO 2018/188708 A1 | 10/2018 |
| WO | WO 2018/188709 A1 | 10/2018 |
| WO | WO 2018/188710 A1 | 10/2018 |
| WO | WO 2018/201152 A1 | 11/2018 |
| WO | WO 2018/204767 A1 | 11/2018 |
| WO | WO 2018/210391 A1 | 11/2018 |
| WO | WO 2018/226417 A1 | 12/2018 |
| WO | WO 2018/227066 A1 | 12/2018 |
| WO | WO 2019/005836 A1 | 1/2019 |
| WO | WO 2019/014344 A1 | 1/2019 |
| WO | WO 2019/034221 A1 | 2/2019 |
| WO | WO 2019/034222 A1 | 2/2019 |
| WO | WO 2019/040694 A1 | 2/2019 |
| WO | WO 2019/051412 A1 | 3/2019 |
| WO | WO 2019/057256 A1 | 3/2019 |
| WO | WO 2019/083839 A1 | 5/2019 |
| WO | WO 2019/089875 A1 | 5/2019 |
| WO | WO 2019/090239 A1 | 5/2019 |
| WO | WO 2019/091526 A1 | 5/2019 |
| WO | WO 2019/091527 A1 | 5/2019 |
| WO | WO 2019/091528 A1 | 5/2019 |
| WO | WO 2019/091529 A1 | 5/2019 |
| WO | WO 2019/091532 A1 | 5/2019 |
| WO | WO 2019/094635 A1 | 5/2019 |
| WO | WO 2019/097288 A1 | 5/2019 |
| WO | WO 2019/099662 A1 | 5/2019 |
| WO | WO 2019/099845 A1 | 5/2019 |
| WO | WO 2019/099975 A2 | 5/2019 |
| WO | WO 2019/108337 A1 | 6/2019 |
| WO | WO 2019/113077 A1 | 6/2019 |
| WO | WO 2019/113203 A1 | 6/2019 |
| WO | WO 2019/120424 A1 | 6/2019 |
| WO | WO 2019/120425 A1 | 6/2019 |
| WO | WO 2019/120427 A1 | 6/2019 |
| WO | WO 2019/120428 A1 | 6/2019 |
| WO | WO 2019/120429 A1 | 6/2019 |
| WO | WO 2019/120430 A1 | 6/2019 |
| WO | WO 2019/120431 A1 | 6/2019 |
| WO | WO 2019/120432 A1 | 6/2019 |
| WO | WO 2019/120433 A1 | 6/2019 |
| WO | WO 2019/120434 A1 | 6/2019 |
| WO | WO 2019/120435 A1 | 6/2019 |
| WO | WO 2019/120436 A1 | 6/2019 |
| WO | WO 2019/120437 A1 | 6/2019 |
| WO | WO 2019/120438 A1 | 6/2019 |
| WO | WO 2019/120439 A1 | 6/2019 |
| WO | WO 2019/120440 A1 | 6/2019 |
| WO | WO 2019/120441 A1 | 6/2019 |
| WO | WO 2019/120442 A1 | 6/2019 |
| WO | WO 2019/120443 A1 | 6/2019 |
| WO | WO 2019/120444 A1 | 6/2019 |
| WO | WO 2019/120445 A1 | 6/2019 |
| WO | WO 2019/120446 A1 | 6/2019 |
| WO | WO 2019/120447 A1 | 6/2019 |
| WO | WO 2019/120448 A1 | 6/2019 |
| WO | WO 2019/120450 A1 | 6/2019 |
| WO | WO 2019/120451 A1 | 6/2019 |
| WO | WO 2019/120452 A1 | 6/2019 |
| WO | WO 2019/120453 A1 | 6/2019 |
| WO | WO 2019/120458 A1 | 6/2019 |
| WO | WO 2019/123003 A1 | 6/2019 |
| WO | WO 2019/123004 A1 | 6/2019 |
| WO | WO 2019/123005 A1 | 6/2019 |
| WO | WO 2019/134726 A1 | 7/2019 |
| WO | WO 2019/149330 A1 | 8/2019 |
| WO | WO 2019/161859 A1 | 8/2019 |
| WO | WO 2019/161860 A1 | 8/2019 |
| WO | WO 2019/161861 A1 | 8/2019 |
| WO | WO 2019/161862 A1 | 8/2019 |
| WO | WO 2019/161863 A1 | 8/2019 |
| WO | WO 2019/174687 A1 | 9/2019 |
| WO | WO 2019/174692 A1 | 9/2019 |
| WO | WO 2019/174693 A1 | 9/2019 |
| WO | WO 2019/174694 A1 | 9/2019 |
| WO | WO 2019/174695 A1 | 9/2019 |
| WO | WO 2019/174696 A1 | 9/2019 |
| WO | WO 2019/174697 A1 | 9/2019 |
| WO | WO 2019/174698 A1 | 9/2019 |
| WO | WO 2019/214787 A1 | 11/2019 |
| WO | WO 2019/214788 A1 | 11/2019 |
| WO | WO 2019/221830 A1 | 11/2019 |
| WO | WO 2019/222644 A1 | 11/2019 |
| WO | WO 2019/222652 A1 | 11/2019 |
| WO | WO 2019/238180 A1 | 12/2019 |
| WO | WO 2019/238181 A1 | 12/2019 |
| WO | WO 2019/238182 A1 | 12/2019 |
| WO | WO 2019/238183 A1 | 12/2019 |
| WO | WO 2019/238195 A1 | 12/2019 |
| WO | WO 2019/238196 A1 | 12/2019 |
| WO | WO 2019/238197 A1 | 12/2019 |

(56) References Cited

FOREIGN PATENT DOCUMENTS

| WO | WO 2019/238198 A1 | 12/2019 |
|---|---|---|
| WO | WO 2019/242828 A1 | 12/2019 |
| WO | WO 2019/245679 A1 | 12/2019 |
| WO | WO 2020/007429 A1 | 1/2020 |
| WO | WO 2020/007430 A1 | 1/2020 |
| WO | WO 2020/015804 A1 | 1/2020 |
| WO | WO 2020/035121 A1 | 2/2020 |
| WO | WO 2020/048576 A1 | 3/2020 |
| WO | WO 2020/051548 A1 | 3/2020 |
| WO | WO 2020/055998 A1 | 3/2020 |
| WO | WO 2020/057705 A1 | 3/2020 |
| WO | WO 2020/076501 A1 | 4/2020 |
| WO | WO 2020/076605 A2 | 4/2020 |
| WO | WO 2020/076607 A1 | 4/2020 |
| WO | WO 2020/076609 A1 | 4/2020 |
| WO | WO 2020/086302 A1 | 4/2020 |
| WO | WO 2020/076605 A3 | 5/2020 |
| WO | WO 2020/103996 A1 | 5/2020 |
| WO | WO 2020/106812 A1 | 5/2020 |
| WO | WO 2020/106822 A1 | 5/2020 |
| WO | WO 2020/112289 A1 | 6/2020 |
| WO | WO 2020/123771 A2 | 6/2020 |
| WO | WO 2020/125906 A1 | 6/2020 |
| WO | WO 2020/125907 A1 | 6/2020 |
| WO | WO 2020/125908 A1 | 6/2020 |
| WO | WO 2020/131561 A1 | 6/2020 |
| WO | WO 2020/142185 A1 | 7/2020 |
| WO | WO 2020/156624 A1 | 8/2020 |
| WO | WO 2020/156625 A1 | 8/2020 |
| WO | WO 2020/156626 A1 | 8/2020 |
| WO | WO 2020/160738 A1 | 8/2020 |
| WO | WO 2020/169162 A1 | 8/2020 |
| WO | WO 2020/173531 A1 | 9/2020 |
| WO | WO 2020/173534 A1 | 9/2020 |
| WO | WO 2020/210815 A1 | 10/2020 |
| WO | WO 2020/220024 A1 | 10/2020 |
| WO | WO 2020/220025 A1 | 10/2020 |
| WO | WO 2020/220026 A1 | 10/2020 |

OTHER PUBLICATIONS

Bridgville Plastics Inc., "NUVAL Continent Ostomy Valve Model 3985 Instruction Manual," 10 pages, believed to be publicly available before Dec. 30, 2014.

Dale, M., et al., "The Effect of Cold Therapy on Pain, Swelling, and Range of Motion after Anterior Cruciate Ligament Reconstructive Surgery," Arthroscopy: The Journal of Arthroscopic & Related Surgery, vol. 10, Issue 5, Oct. 1994, pp. 530-533.

Faller et al., "The MIC-KEY," Ostomy Wound Manage, 38(3):50-53, Apr. 1992.

GhaseelCom Jo, by Oioo, app704.com, last updated Jul. 17, 2018 (retrieved on Dec. 30, 2019), retrieved from the Internet, https://www.app704.com/1272706062.

Hunter, Tim B., et al., "Medical Devices of the Abdomen and Pelvis," RadioGraphics 2005; 25:503-523.

Legacy Flext Alerts, appadvice.com (online), last updated Oct. 26, 2018 (retrieved on Dec. 30, 2018), retrieved from the Internet, https://appadvice.com/app/legacy-flex-alert/869412041.

Setaku: Laundry On-Demand!, by Han, behance.net (online), published on Sep. 7, 2015 (retrieved on Dec. 30, 2019), retrieved from the Internet, https://www.behance.net/gallery/30159963/Setaku-Laundry-on-demand?tracking_source=project_owner_other_projects.

Soliani et al., "Colostomy plug devices: a possible new approach to the problem of incontinence," Dis Colon Rectum., 35(10):969-974, Oct. 1992.

Wikipedia, "List of polyurethane applications," https://en.wikipedia.org/wiki/List_of_polyurethane_applications, Jun. 19, 2019, in 12 pages.

International Search Report in corresponding International Patent Application No. PCT/US2021/071891, dated Feb. 2, 2022, in 10 pages.

\* cited by examiner

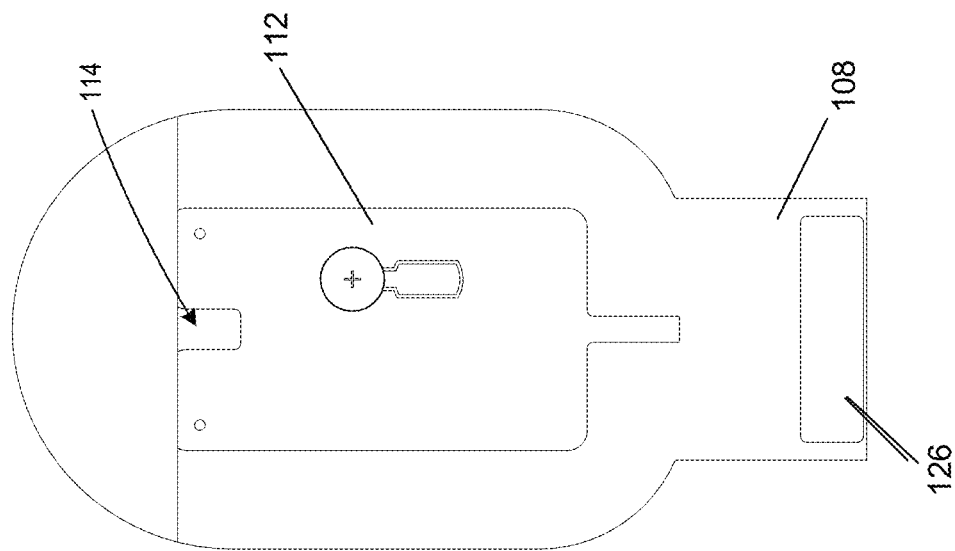
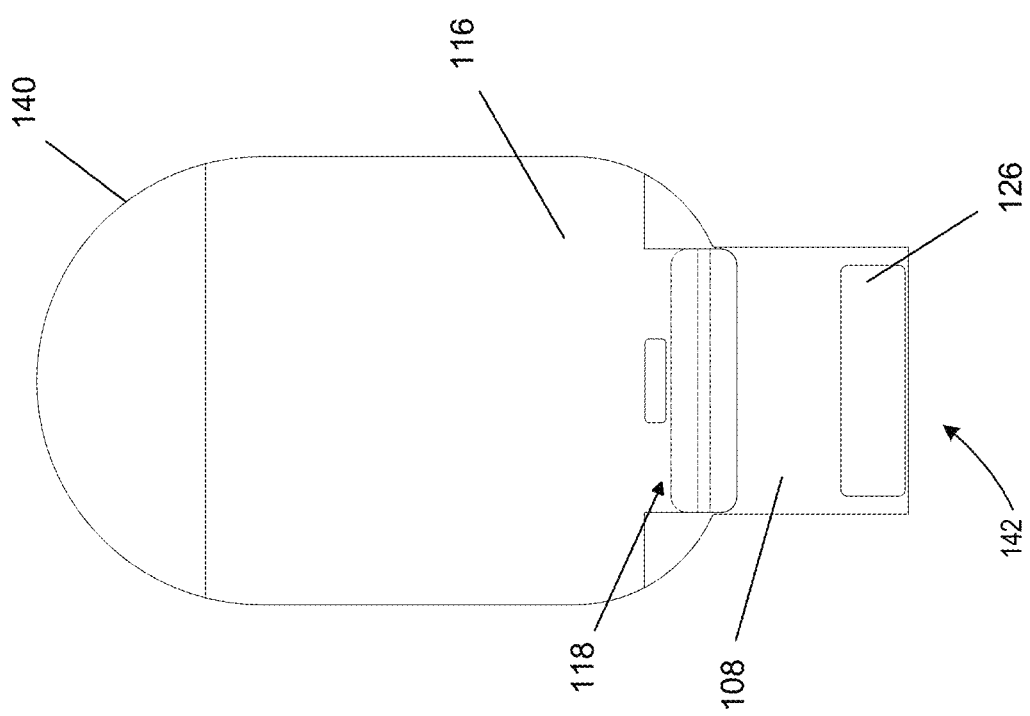
FIG. 2B
FIG. 2A

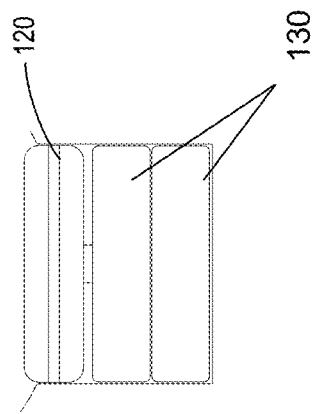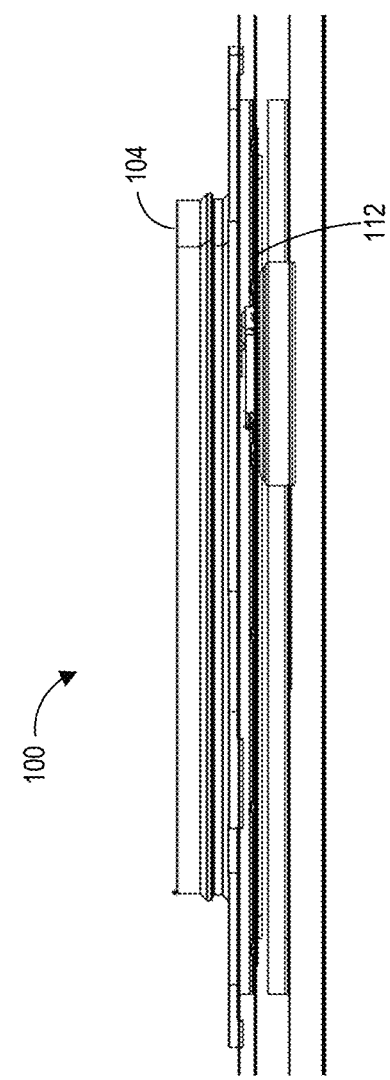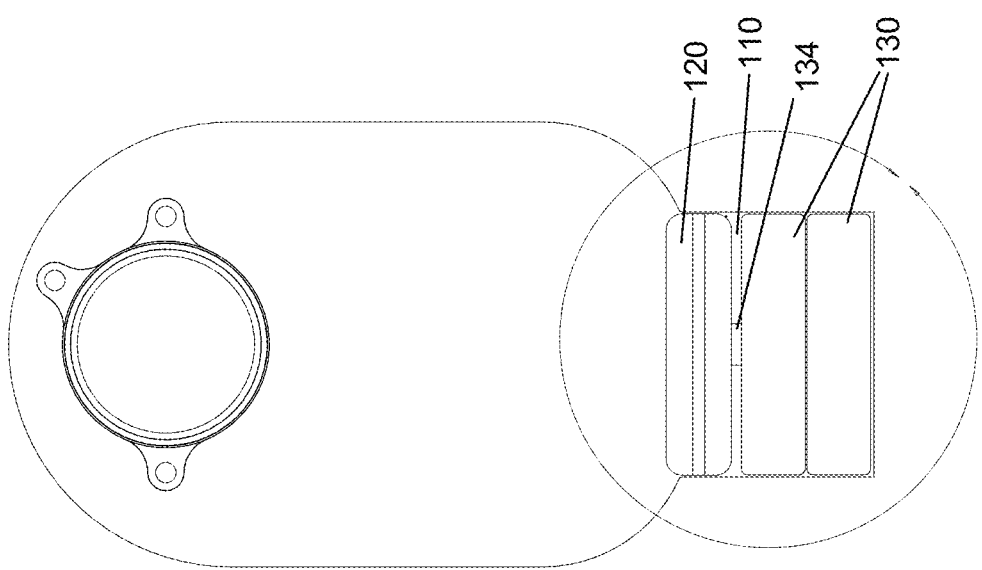

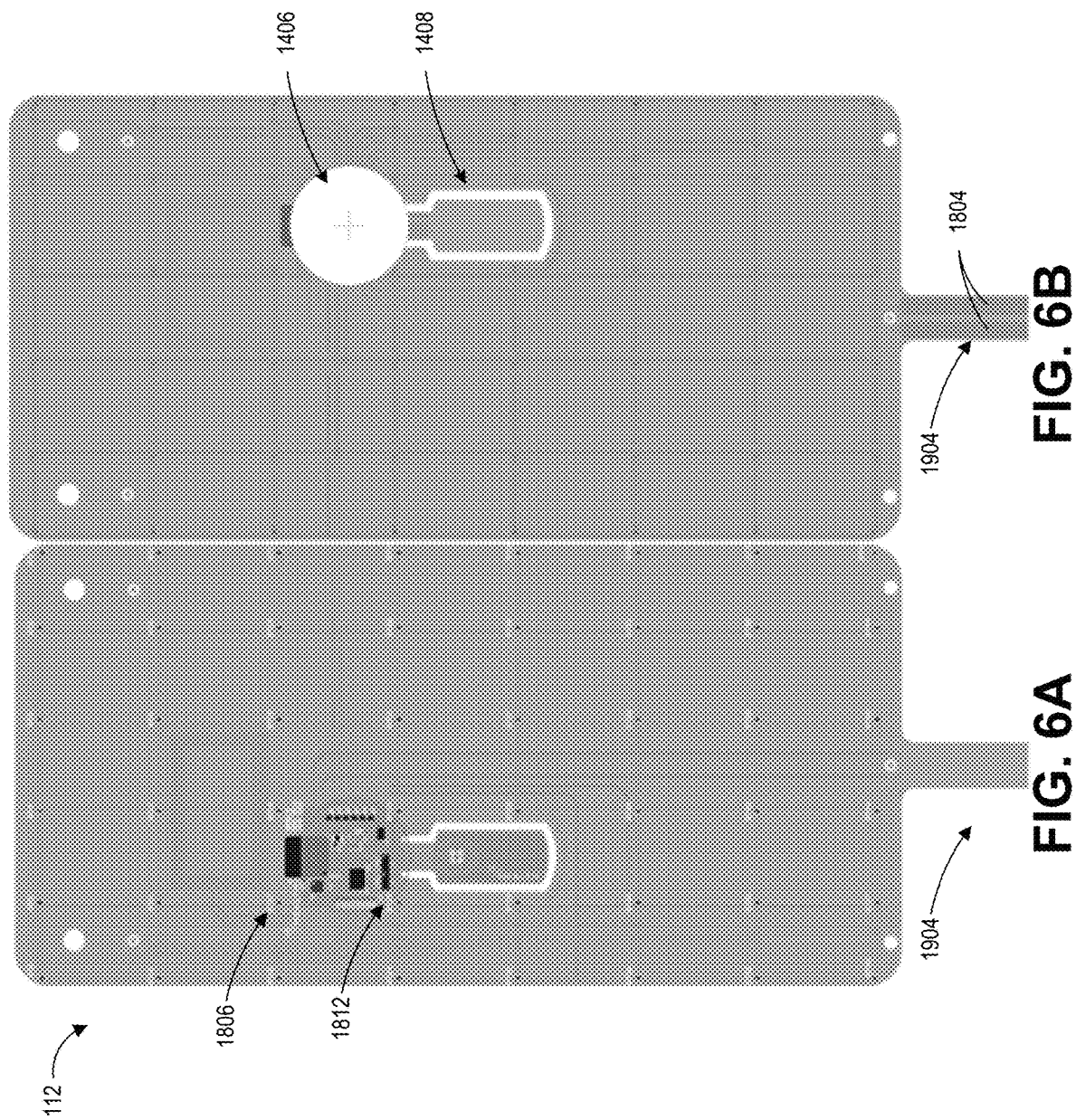

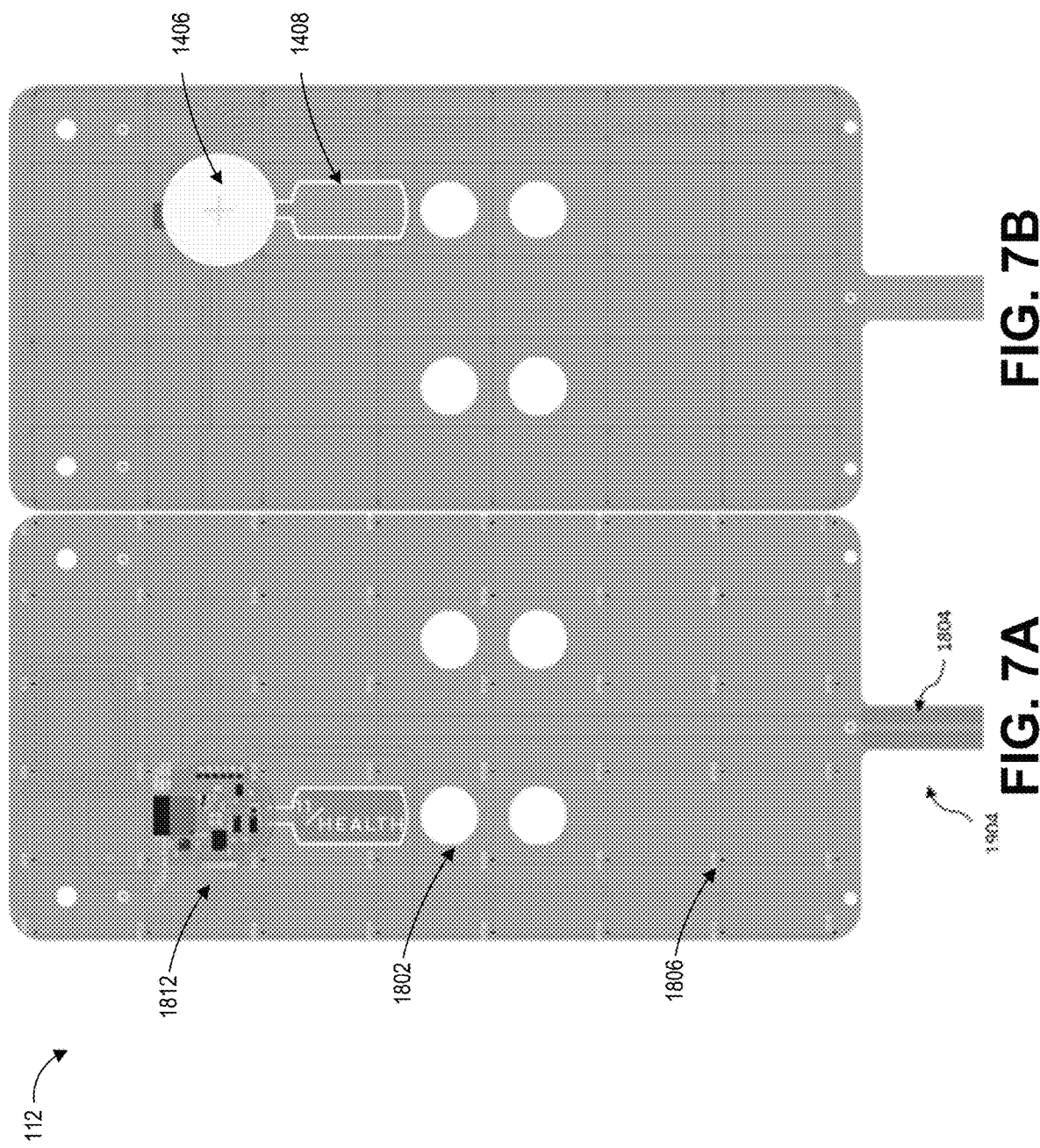

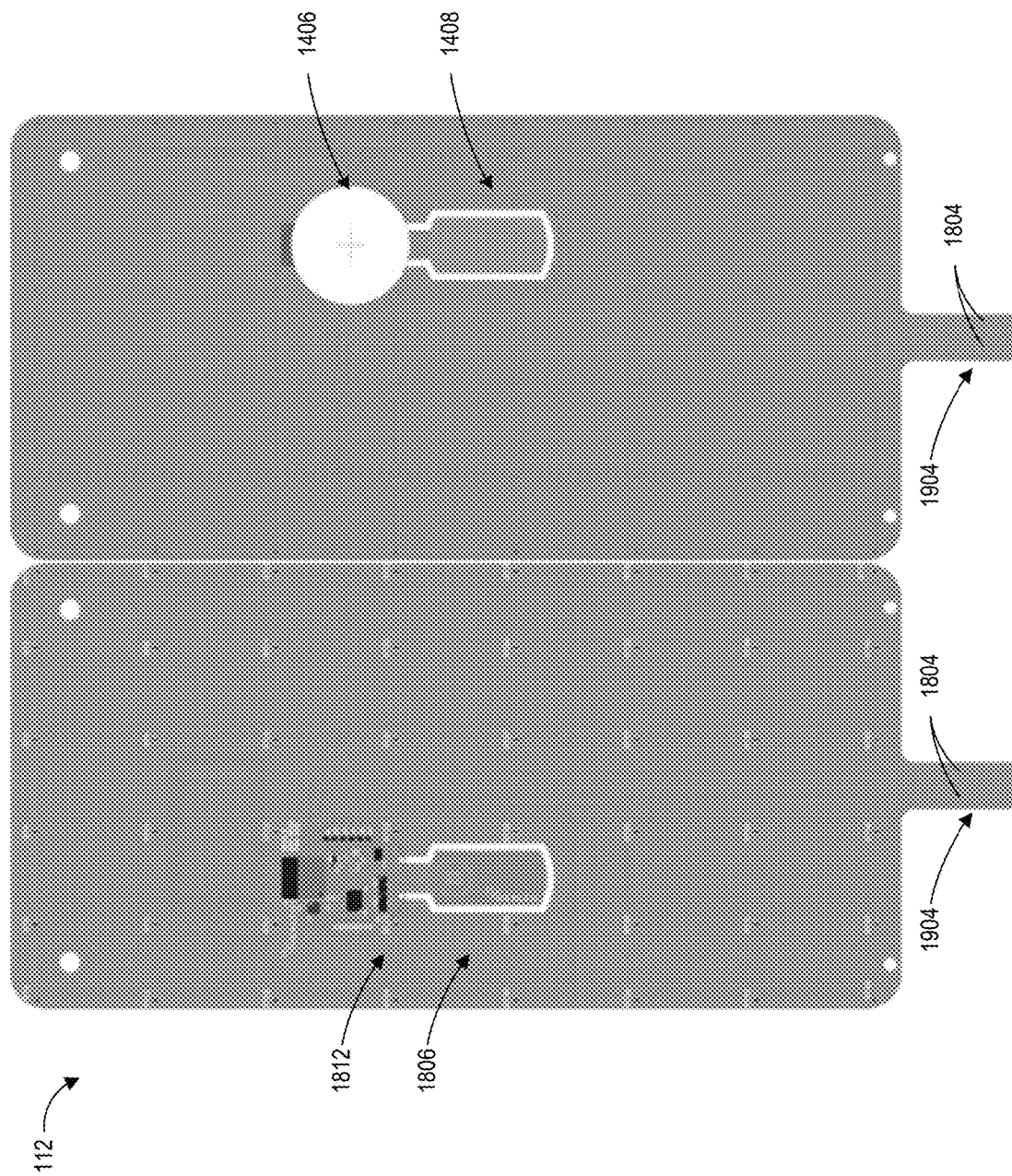

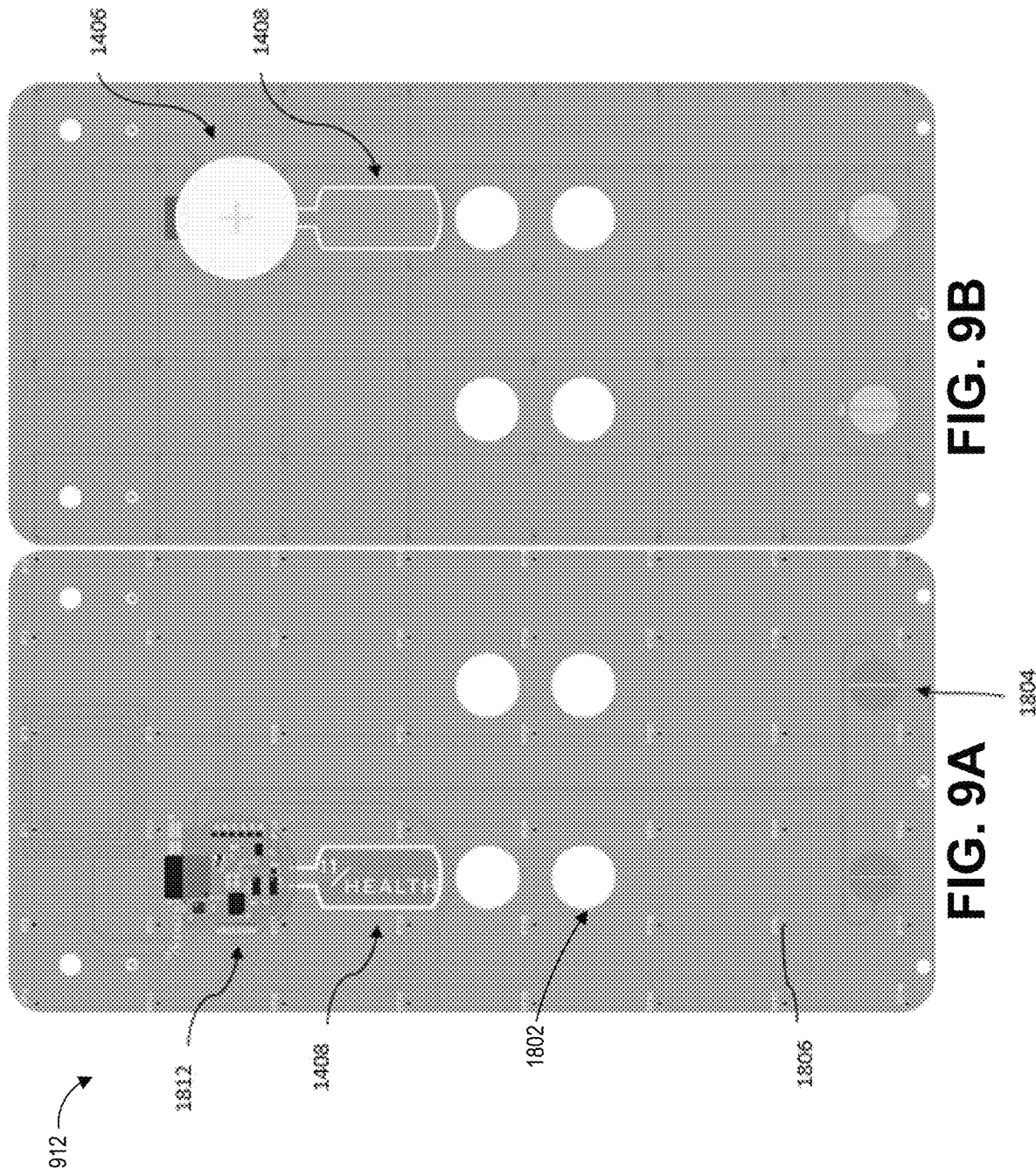

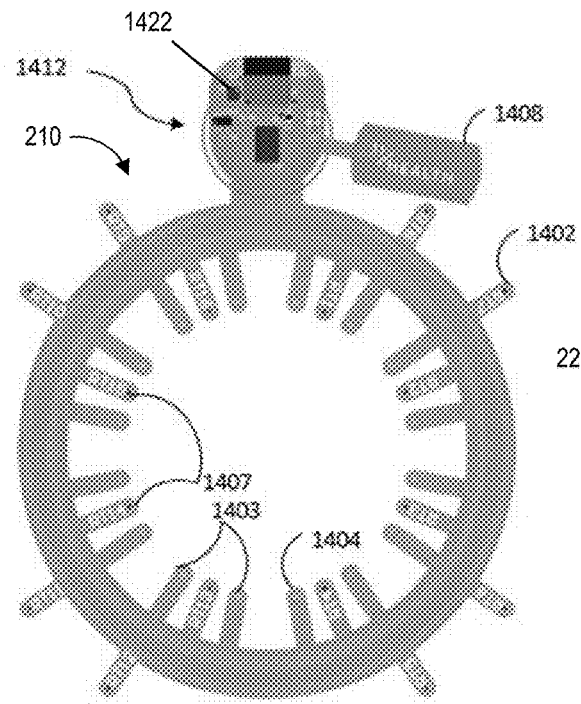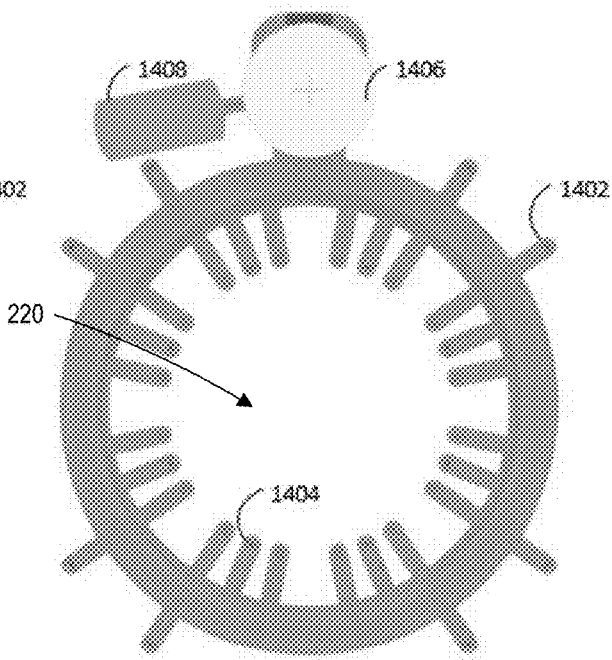
FIG. 14A  FIG. 14B
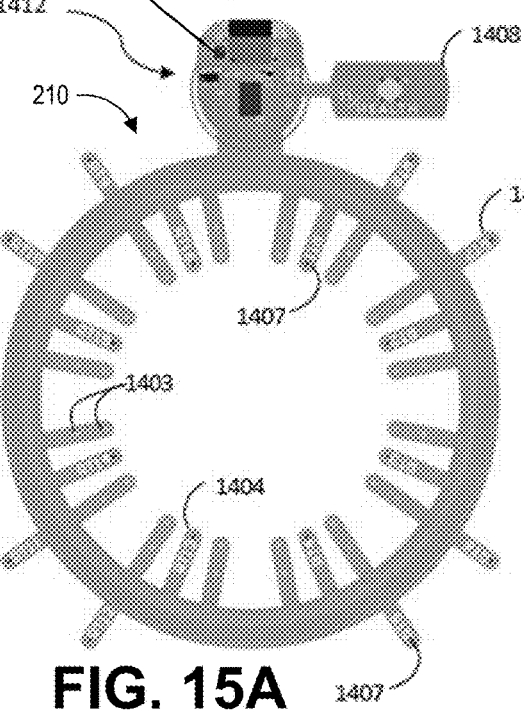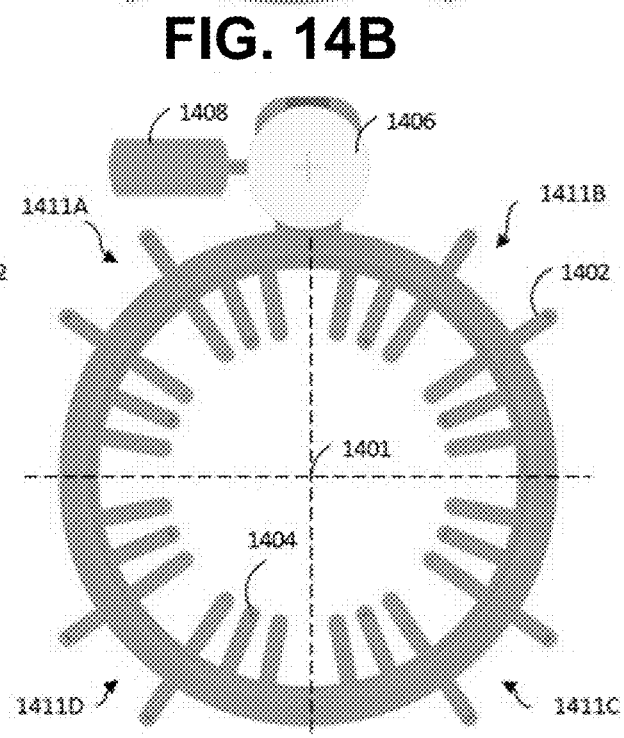
FIG. 15A  FIG. 15B

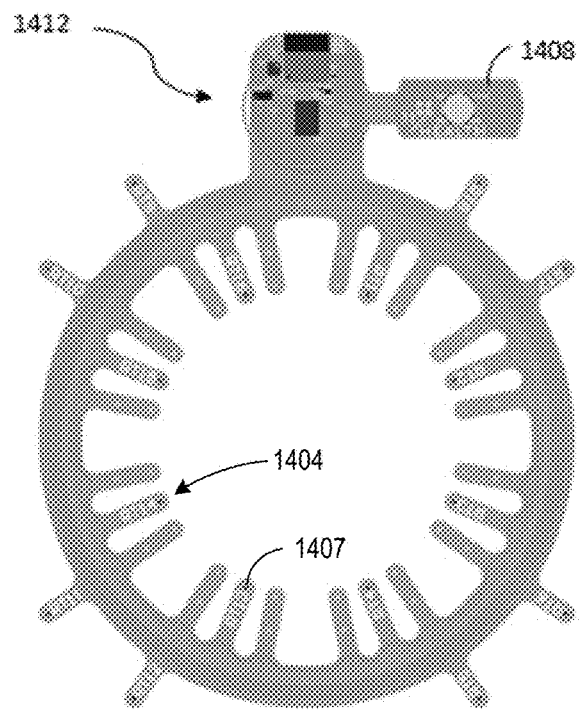
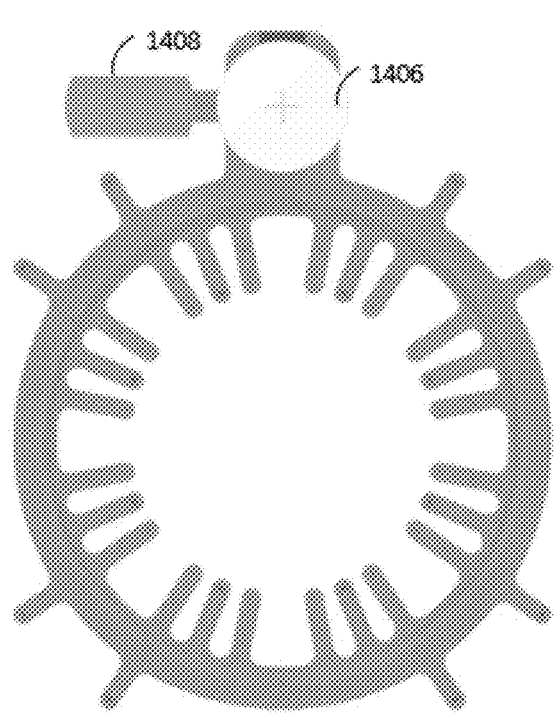
FIG. 17A  FIG. 17B
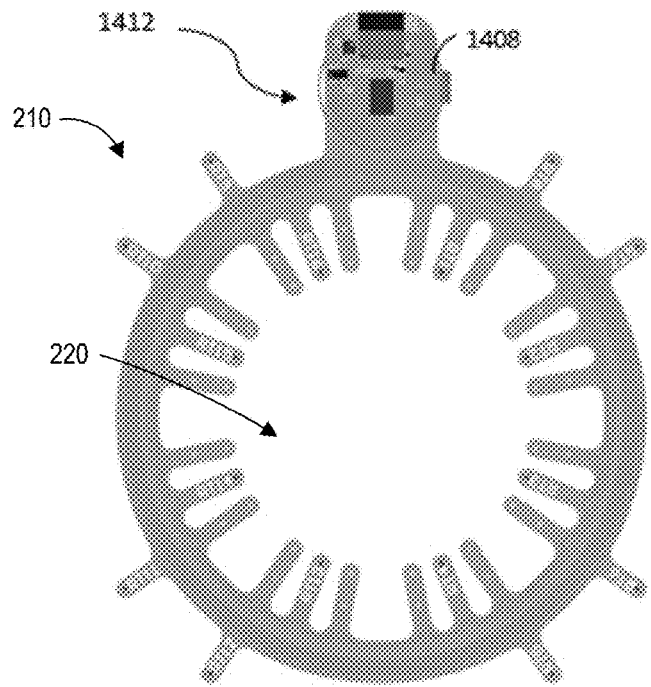
FIG. 17C

OSTOMY SYSTEMS AND METHODS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application claims the priority benefit of U.S. Provisional Application No. 63/092,437, filed Oct. 15, 2020, the entirety of which is incorporated herein by reference and should be considered a part of this specification.

RELATED APPLICATIONS

This application is related to U.S. Patent Application Publication Nos. 2019/0133810, 2019/0133811, 2019/0133812, and 2020/0188161. The disclosure of each related application is incorporated herein by reference in its entirety and should be considered a part of this specification. The embodiments described in this application are compatible with and can be part of the embodiments described in the related applications, and some or all of the features described in this application can be used or otherwise combined together or with any of the features described in the related applications.

BACKGROUND

Field

This disclosure describes several different example ostomy bags and wafers that can include sensors and optionally electronics.

Description of the Related Art

An ostomy bag can be a medical bag that collects human waste (either stools, urine, or both) from patients who cannot excrete waste naturally due to medical issues, which include, among others, cancer, trauma, inflammatory bowel disease (IBD), bowel obstruction, infection and fecal incontinence. In such cases, a surgical procedure is performed whereby a waste passage is created. This waste passage can be the ureter (called an urostomy), the small bowel or ileum (called an ileostomy, part of the small intestine) or the large bowl or colon (called a colostomy, part of the large intestine), which may be diverted to an artificial opening in the abdominal wall, thus resulting in part of the specific internal anatomy, to lie partially outside the body wall. This procedure can be referred to as an ostomy, and the part of the waste passage which is seen on the outside of the body can be referred to as a stoma.

An ostomy system can include a separate wafer and bag (and thus includes a coupling mechanism, such as an attachment or flange). The bag can be disposed without having to take off the wafer from the user's body.

SUMMARY

An ostomy bag according to the present disclosure can include: two bag layers permanently joined together around a portion of an edge of the bag layers, a remainder of the edge of the bag layers remaining open to define a drain opening, a first one of the bag layers configured to be placed facing skin of a user and a second one of the bag layers configured to face away from the user when the first one of the bag layers faces the skin of the user; a stoma opening in the first wall, the stoma opening configured to be disposed around a stoma of the user and to receive effluent from the stoma; and a flexible sensor layer, the flexible sensor layer comprising a hardware processor and a coin cell battery, wherein the hardware processor is supported by the coin cell battery.

In a configuration, the coin cell battery of the ostomy bag can be attached to the hardware processor and/or the sensor layer by electrically conductive adhesive.

In a configuration, at least a portion of the hardware processor can be located close to a center of the coin cell battery to reduce component detaching during flexing of the ostomy bag.

In a configuration, the sensor layer may not include a printed circuit board.

In a configuration, the hardware processor can be located on a user-facing side of the sensor layer and the coin cell battery is on an opposite side of the sensor layer facing away from the user.

In a configuration, the sensor layer can comprise a plurality of openings to improve flexibility of the sensor layer.

In a configuration, the sensor layer can further comprise a plurality of temperature sensors.

In a configuration, the temperature sensors can be arranged in an array or matrix.

In a configuration, the hardware processor can be configured to detect a fill level of the bag or an output volume at least in part based on signals from the temperature sensors.

In a configuration, the sensor layer can comprise a cut-out portion or slot configured to define a viewing window for observing the stoma.

In a configuration, an outermost layer of the bag can comprise a gap or opening aligning with the cut-out portion or slot.

In a configuration, the ostomy bag can further comprise comfort layers on both sides of the bag layers, the comfort layers defining outermost layers of the bag.

In a configuration, the sensor layer can be located between one of the comfort layers and the second bag layer.

In a configuration, the sensor layer can be protected from the one of the comfort layers by a clear protector layer.

An ostomy bag according to the present disclosure can be part of an ostomy kit that comprises a predetermined number of new ostomy bags. The ostomy bag can include: two bag layers permanently joined together around a portion of an edge of the bag layers, a remainder of the edge of the bag layers remaining open to define a drain opening, a first one of the bag layers configured to be placed facing skin of a user and a second one of the bag layers configured to face away from the user when the first one of the bag layers faces the skin of the user; a stoma opening in the first bag layer, the stoma opening configured to be disposed around a stoma of the user and to receive effluent from the stoma; a connector located near the drain opening, the connector comprising a first part on a first side of the bag facing skin of the user and a second part located on an opposite second side of the bag facing away from the user, the first and second parts being complementary to each other so that when a portion of the bag near the drain opening is folder over, the first part can be releasably secured onto the second part to seal the bag; a hardware processor; and a sensor layer, the sensor layer comprising a sensor near the drain opening, the sensor configured to output a signal to the processor when the first part is attached to the second part of the connector for the first time, wherein the hardware processor is configured to wirelessly communicate to a remote server a message that the ostomy bag is used in response to the signal from the sensor, and wherein a processor on the remote server is configured to decrease the predetermined number of new ostomy bags by one in response to the message.

In a configuration, the hardware processor of the bag or the processor of the remote server can be configured to alert the user when the number of new ostomy bags remaining in the kit has decreased to a threshold.

In a configuration, the hardware processor of the bag or the processor of the remote server can be further configured to prompt the user to order new ostomy bags in response to the number of new ostomy bags remaining in the kit reaching threshold.

In a configuration, the hardware processor of the bag or the processor of the remote server can be further configured to automatically initiate an order of new ostomy bags in response to the number of new ostomy bags remaining in the kit reaching threshold.

In a configuration, the sensor can be further configured to detect subsequent detachment of the first part from the second part of the connector so as to detect a drain event.

In a configuration, the hardware processor of the bag or the processor of the remote server can be configured to detect trends in the number of drain events.

In a configuration, the hardware processor of the bag or the processor of the remote server can be configured to output an alert when the user's drain events have increased or decreased from a baseline that is determined from the trends.

In a configuration, the connector can comprise a metallic component.

In a configuration, the sensor can comprise one or more electrodes.

In a configuration, the one or more electrodes can be located on a drain tab of the sensor layer, the drain tab extending away from a main body of the sensor layer toward the drain opening of the bag.

In a configuration, the one or more electrodes can be located on a user-facing side of the sensor layer.

In a configuration, the one or more electrodes can be located on a side of the sensor layer facing away from the user.

In a configuration, the ostomy bag can further comprise comfort layers on both sides of the bag layers, the comfort layers defining outermost layers of the bag.

In a configuration, the sensor layer can be located between one of the comfort layers and the second bag layer.

In a configuration, the sensor layer can be protected from the one of the comfort layers by a clear protector layer.

In a configuration, the first part of the connector can be located on a user-facing side of the clear protector layer.

In a configuration, the connector can comprise interlocking zippers.

An ostomy wafer according to the present disclosure can be configured to couple an ostomy bag to a user. The wafer can comprise: a sensor layer comprising at least in part a ring-shaped main body and a plurality of inner fingers extending radially inwardly from the main body; a plurality of sensors located on the plurality of inner fingers, the plurality of sensors comprising leak sensors and temperature sensors; and a hardware processor, the hardware processor configured to detect at least one of user skin temperature or leakage of effluent based at least in part on signals from one or more of the plurality of sensors.

In a configuration, the ostomy wafer can further comprise a battery configured to power the plurality of sensors.

In a configuration, the plurality of leak sensors can be configured to be separated into four quadrants.

In a configuration, each leak sensor can comprise a ground electrode and a sensing electrode.

In a configuration, each leak sensor can be located on one of the inner fingers, the ground electrode being further away from a tip of the one of fingers than the sensing electrode.

In a configuration, the plurality of inner fingers can form a plurality of sensing regions, each sensing region comprising one inner finger with a temperature sensor between two inner fingers with leak sensors.

In a configuration, the hardware processor can be configured to detect inflammation of the user based at least in part on signals from the temperature sensors on the inner fingers.

In a configuration, the ostomy wafer sensor layer can further comprise outer fingers extending radially outwardly from the main body.

In a configuration, the ostomy wafer can further comprise a plurality of temperature sensors located on the outer fingers.

In a configuration, the hardware processor can be configured to detect peeling of the wafer from the user's body based at least in part on signals from the plurality of temperature sensors on the outer fingers.

In a configuration, the ostomy wafer can further comprise an accelerometer.

In a configuration, the hardware processor can be further configured to determine a location of a leak and/or inflammation based on at least one signal from at least one of the leak and/or temperature sensors, and data from the accelerometer.

An ostomy wafer according to the present disclosure can be configured to couple an ostomy bag to a user. The wafer can comprise: a sensor layer comprising a plurality of leak sensors surrounding a stoma opening of the wafer, wherein the plurality of leak sensors are generally an equal distance away from a center of the stoma opening; and a hardware processor, the hardware processor configured to detect leakage of effluent based at least in part on signals from one or more of the plurality of leak sensors, the leak sensors being in an open-circuit configuration, wherein contact with moisture or liquid can be configured to complete a leak detection circuit.

In a configuration, the hardware processor can be configured to determine a location of a leak based at least in part on a location of at least one leak sensor that is in a closed circuit.

In a configuration, the hardware processor can be configured to receive a voltage value of one or more leak sensors so as to determine whether any leak sensor or any group of leak sensors is in a closed circuit.

In a configuration, the hardware processor can be configured to normalize the voltage value by a battery voltage value.

In a configuration, the hardware processor can be further configured to determine a rate of change of the voltage value so as to determine whether any leak sensor or any group of leak sensors is in a closed circuit.

In a configuration, the hardware processor can be further configured to differentiate moisture due to the user's sweating or leakage of effluent.

In a configuration, the plurality of leak sensors can be configured to be separated into four groups.

In a configuration, the ostomy wafer can comprise an accelerometer.

In a configuration, the hardware processor can be further configured to determine a location and/or direction of a leak based on at least one signal from at least one of the leak sensors and data from the accelerometer.

In a configuration, the ostomy wafer can further comprise a user adhesive layer, the user adhesive layer comprising one or more openings configured to overlap with one or more of the leak sensors.

In a configuration, the one or more openings can have an inner diameter greater than an outer diameter of the leak sensors.

An ostomy wafer according to the present disclosure can be configured to couple an ostomy bag to a user. The wafer can comprise: a sensor layer comprising a plurality of temperature sensors surrounding a stoma opening of the wafer, wherein the plurality of temperature sensors can be configured to be separated into four quadrants; and a hardware processor, the hardware processor configured to detect inflammation based at least in part on signals from one or more of the plurality of temperature sensors, wherein the hardware processor can be configured to determine an average temperature of the temperature sensors in the same quadrant.

In a configuration, the hardware processor can be further configured to calculate a difference between a short-term average temperature and a long-term average temperature of the temperature sensors in the same quadrant.

In a configuration, the hardware processor can be further configured to calculate a rate of change of a different between the short-term and long-term average temperatures.

In a configuration, the sensor layer can comprise at least in part a ring-shaped main body and a plurality of fingers extending radially inwardly from the main body, the plurality of temperature sensors located on the plurality of fingers.

In a configuration, the ostomy wafer can further comprise an accelerometer.

In a configuration, the hardware processor can be further configured to determine a location of inflammation based on at least one signal from at least one of the temperature sensors and data from the accelerometer.

BRIEF DESCRIPTION OF THE DRAWINGS

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure. Corresponding numerals indicate corresponding parts. Any dimensions on the drawings are example dimensions and not meant to be limiting. With reference to an ostomy system, the front side is the side facing away from a user's body and the back side is the side facing toward the user's body. Any features of the ostomy bag examples can be incorporated into any other examples of the ostomy bag disclosed herein. Any features of the ostomy wafer examples can be incorporated into any other ostomy wafer examples disclosed herein.

FIGS. 2A-2B illustrate front views of the example ostomy bag of FIG. 1, with various components hidden for purpose of clarity.

FIG. 3A illustrates a back view of the example ostomy bag of FIG. 1.

FIG. 3B illustrates a detailed view of a bag sealing mechanism of the ostomy bag of FIG. 1.

FIG. 4 illustrates a top view of the example ostomy bag of FIG. 1.

FIGS. 6A-9B illustrate back and front views of various other configurations of a sensor layer of an ostomy bag.

FIGS. 12A-17C illustrate various configurations of an example sensor layer of a wafer or baseplate of an ostomy system.

DETAILED DESCRIPTION

Those of skill in the art will appreciate based on the disclosure herein that the disclosure extends beyond the specifically disclosed embodiments and/or uses and obvious modifications and equivalents thereof. Thus, it is intended that the scope of the disclosure should not be limited by any particular embodiments described herein.

Figure 11A:
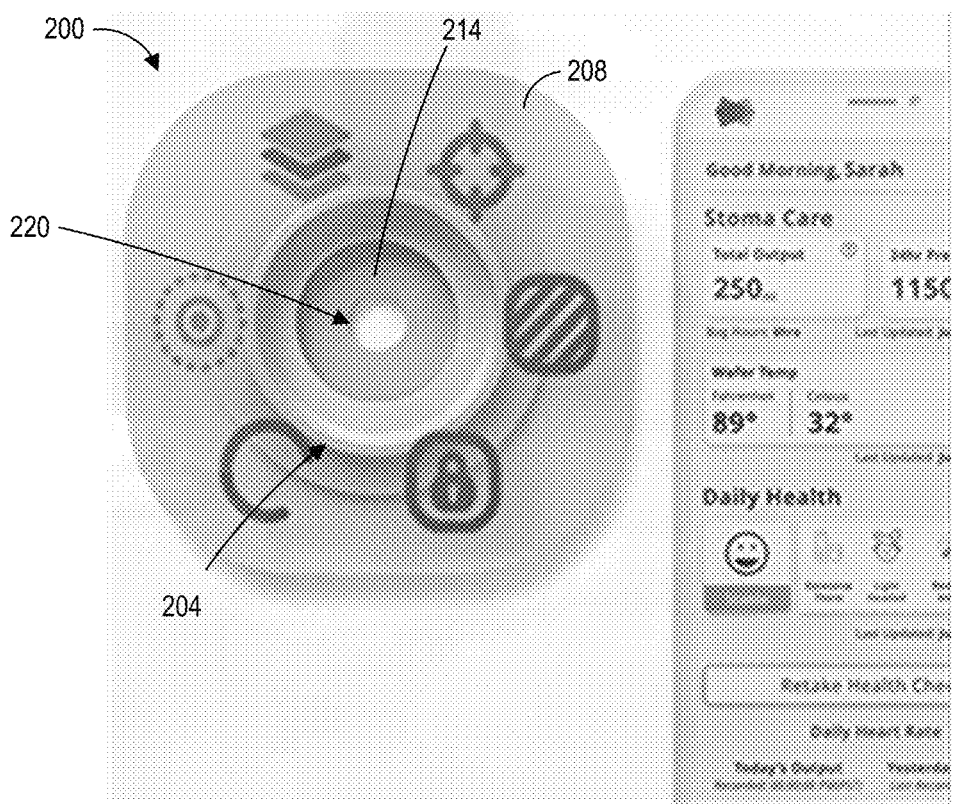
FIG. 11A illustrates a front view of an example wafer or baseplate of an ostomy system.

An ostomy bag according to the present disclosure can include any combinations of sensors, biomarkers (for example, for cancer cells, blood, and the like), and/or electronics. In some configurations, a medical kit can include three groups of any of the ostomy bags disclosed herein, a first group of ostomy bags that are diagnostic bags, a second group of ostomy bags that are analytics bags, and a third group of ostomy bags that are maintenance bags. All the ostomy bags in the medical kit can include electronics and sensors to measure one or more parameters related to the stomal output, also referred to as effluent. The bags can be in electrical communication with a user device, such as a smartphone (for example, as shown in FIG. 11A) or a computer. A user and/or a clinician can monitor (for example, remotely) the use of the ostomy bags and the user's stoma conditions.

A diagnostic bag can be worn by a patient after surgery and before being discharged. It can be more critical to monitor a variety of parameters of the patient immediately after a surgery. However, a diagnostic bag can be expensive. Other ostomy bag configurations may allow a user to choose which sensors pertain to their condition and provide a cheaper alternative. Such bag configurations may have fewer, for example, the bare minimum of sensors, such as only temperature sensors in the wafer and/or bag, for advanced patients who may be acclimated to their stoma condition. A simpler and less expensive ostomy bag, such as an analytics bag with fewer sensors, biomarkers and/or electronics than the diagnostic bag, can also be used to monitor phases of the stoma output, skin temperature changes (and thereby skin infections), and/or stoma/output images/sounds via a camera and/or microphone in the electronic hub of the bag or anywhere in a bag (for example, when the bag does not include an electronic hub) in addition to detecting output or effluent volume and leak. The analytics bag can be used a predetermined period of time after the surgery, such as two weeks, one month, three months, six months, twelve months, or any ranges between those values, or after being discharged from the hospital. The patient can also optionally switch to a maintenance bag that includes just sensors and electronics for volume and leak detection. The maintenance bag can also optionally include sensors and electronics for tracking hydration or dehydration of the patient. The patient can switch to the maintenance bag a predetermined time after the surgery, such as three months, six months, nine months, twelve months, eighteen months, twenty-four months, or any range between those values. In some implementations, a medical kit can include one or more of the diagnostic bags, one or more of the analytics bags, and one or more of the maintenance bags.

The ostomy bag and wafer examples disclosed herein can address the needs of patients who may be longer term patients (also known as "established ostomates") as well as patients who have convex needs.

The ostomy bag and wafer examples disclosed herein can improve the experience and quality of life as an ostomate as well as clinical outcomes through providing improved data, insights, and product experience.

Some examples of the example ostomy bags and wafers disclosed herein include one or more of the following non-limiting features:

Remote and/or continuous monitoring of ostomy function, appliance usage and skin condition to provide opportunities for early intervention.

Helping patients understand their own condition better using real time data and/or patient coaching by a clinician or another experienced ostomate, who may not be a medical professional.

Delivering a better patient experience.

The ostomy bag examples (also referred to as a "maintenance bag") disclosed herein can include one or more of the following non-limiting features, such as when compared with existing ostomy bag products such as a diagnostic or analytic bag described above:

A bag constructed from fabrics that can be softer to touch, have quicker drying times, and/or provide greater levels of comfort for everyday wear than fabrics used in existing ostomy bags.

A visualization window to more easily observe the stoma.

A drain closure or bag sealing mechanism providing greater comfort and security, but still easy enough for the patient to operate for hygienic and convenient drainage in small spaces.

Thinner, more flexible and discrete; the bag disclosed herein can be folded, placed under tight clothing or used with an ostomy belt or truss without being readily noticeable and/or without impacting its function.

The bags disclosed herein can track a plurality of events and/or conditions that matter to the user of the bags, including artificial intelligence assisted monitoring, tracks for risk of dehydration, obstruction, leakage, and skin conditions.

The bags disclosed herein can track when they have been used and can notify the patient of the usage tracking, so a patient needs not worry about running out of supplies.

The bags disclosed herein can feature coupling which can provide a secure and comfortable seal for even users with large stomas.

Small-sized electronics form factor (for example, having the largest dimension in the range of about 1 cm to about 4 cm)

More flexible (for example, no printed circuit board (PCB))

Lighter weight

Integrates sensor technology to help keep better track of ostomy care.

The maintenance bag can be used by experienced ostomates, individuals who have had their ostomy for at least 3 months and optionally who do not need to be alerted about when to empty their bag. Therefore, the maintenance bag can contain significantly less electronics than a diagnostic bag or an analysis bag, and can be more discrete under the patient's clothing and capable of greater flexibility. The bag can be folded under the clothes of the wearer without effecting the function of the electronics.

Figure 1:
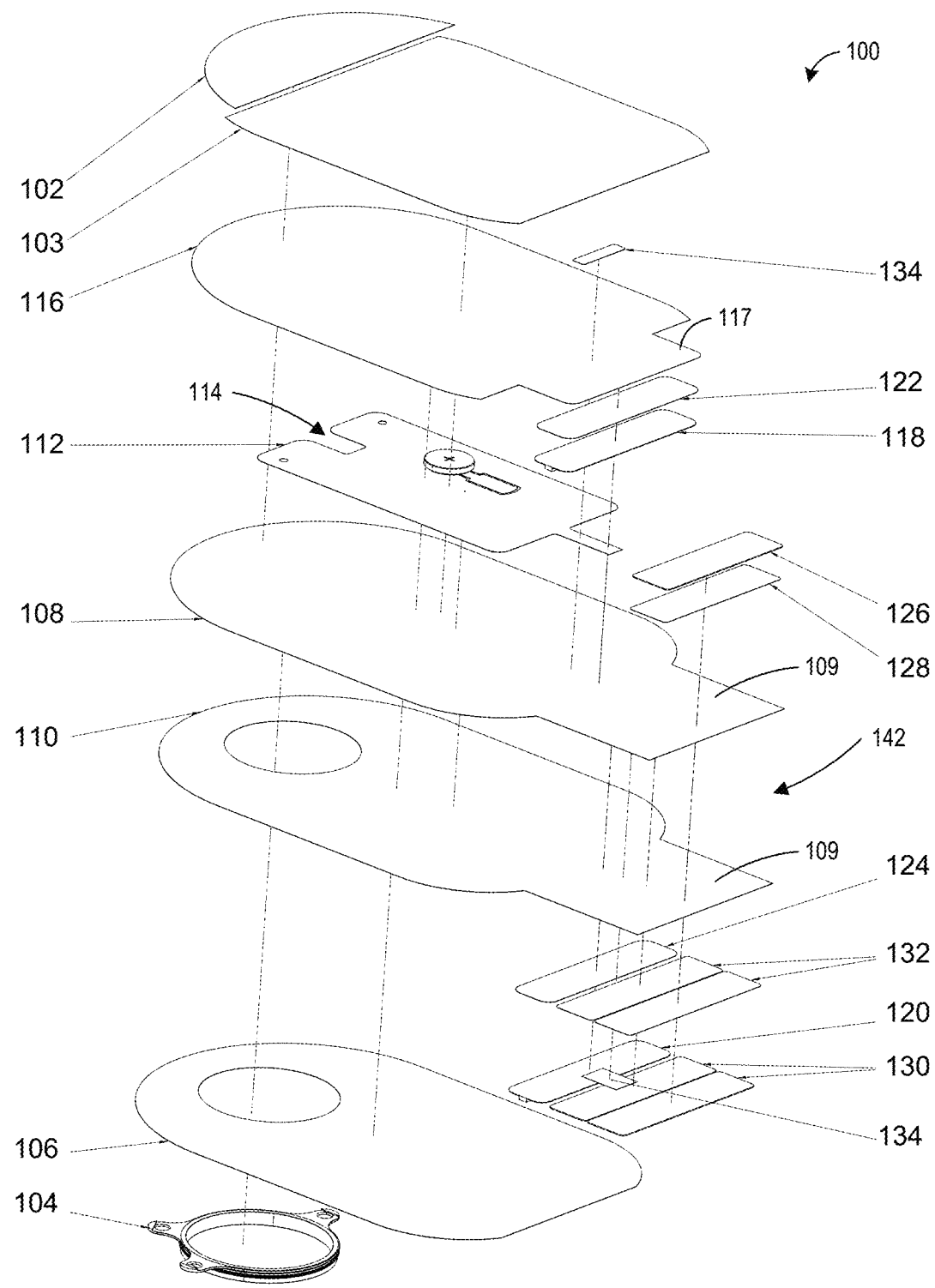
FIG. 1 illustrates an exploded view of an example ostomy bag of an ostomy system without a printed circuit board (PCB).
Figures 5A, 5B:
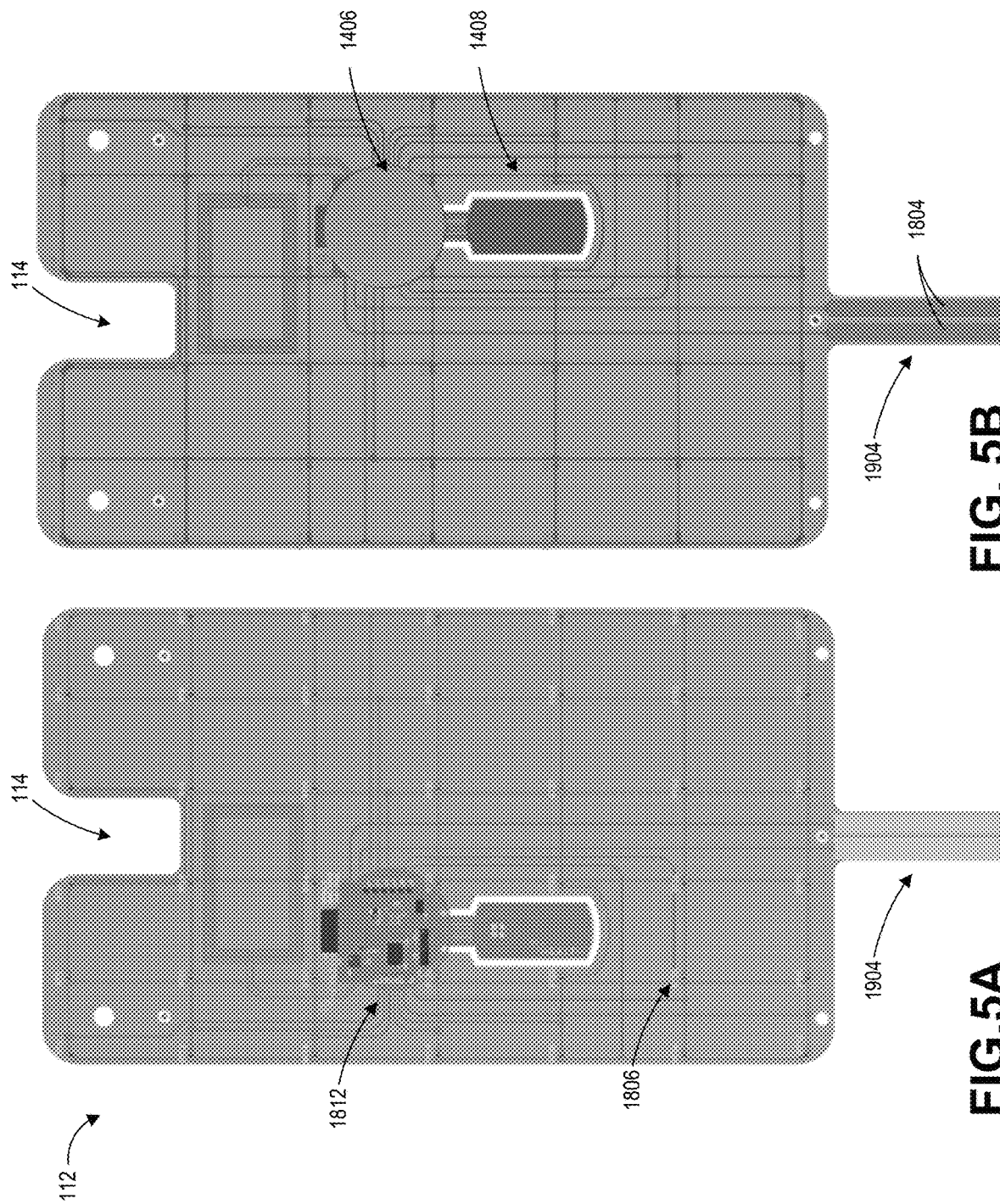
FIGS. 5A-5B illustrate back and front views of an example sensor layer of the ostomy bag of FIG. 1.

FIGS. 1-4 illustrate an example maintenance bag 100 of the present disclosure. The bag 100 can include a plurality of layers. The layers can be welded along the perimeter to form a welded seam 140 except for an opening 142 of the bag 100. The bag 100 can have a front side configured to face away from the user. The bag 100 can have a first comfort layer 102, 103 at the front side. A front surface of the first comfort layer 102, 103 can define the front surface of the bag 100. The first comfort layer 102, 103 can optionally include a top portion 102 and a bottom portion 103 as shown in FIG. 1, or be an integral piece as shown in FIG. 10C. The top and bottom portions 102, 103 can be separated by a gap or opening.

The bag 100 can have a back side opposite the front side such that the back side would face the user during use. The back side of the bag 100 can terminate at a bag coupling component 104 that can couple the bag 100 to a wafer or baseplate, such as the wafer examples disclosed herein or any other suitable wafer. The bag 100 can include a second comfort layer 106 adjacent the bag coupling component 104.

The bag 100 can include an effluent container formed by a first bag film 108 and a second bag film 110. The second bag film 110 can include an opening that can be coupled to the bag coupling component 104. The bag films 108, 110 can be made of EVA (ethylene-vinyl acetate) or any other suitable material. A bag sealing mechanism can be attached to the first and/or second bag films 108, 110 near the bag opening 142 to allow the bag 100 to be releasably closed or sealed, which will be described in greater details below. The bag sealing mechanism can be attached to an extension section 109 of the effluent container.

The bag 100 can include a bag sensor layer 112, which can include sensors and other electronics that will be described in greater details below with reference to FIGS. 5A-9B. The sensor layer 112 can include a cut-out portion or a slot 114 to provide a viewing window to more easily observe the stoma. The slot 114 can extend from a top side of the bag sensor layer 112 toward the bag opening side. The slot 114 can have a length along the length of the bag 100 to allow for a user to view the stoma through the gap or opening in the top comfort layer between the top portion 102 and the bottom portion 103. This allows for the user to more easily align and connect the bag to the wafer, when the wafer is on the user's body. The sensor layer 112 can be separated or protected from the first comfort layer 102, 103 by a plastic sensor protector layer 116. The plastic protector layer 116 can be a clear polyethylene film or be made of any other suitable clear material. In some examples, a bag identification tag 136, for example, a tag containing the serial number of the bag, a barcode, QR code, RFID tag, or the like, can be included between the sensor protector layer 116 and the first comfort layer 102, 103. The user can optionally enter the bag ID or scan the tag 136 using the user device, such as a smartphone. The user, clinician, and/or bag manufacturer can track the bags that have been used based on the entered or scanned bag ID, and/or determine whether the bags are genuine products.

Figure 20A:
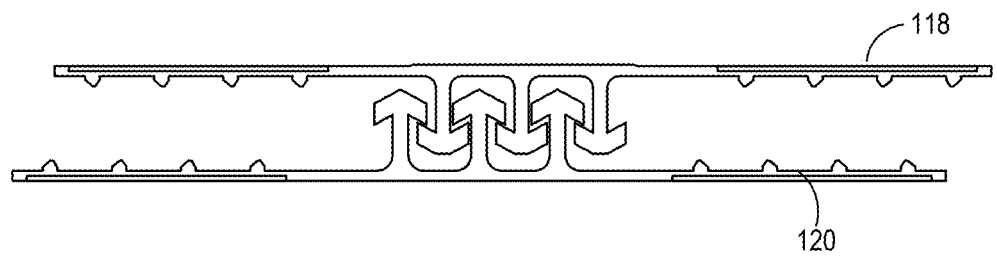
FIG. 20A illustrates an example zipper configuration for sealing an opening of an ostomy bag.
Figure 20B:
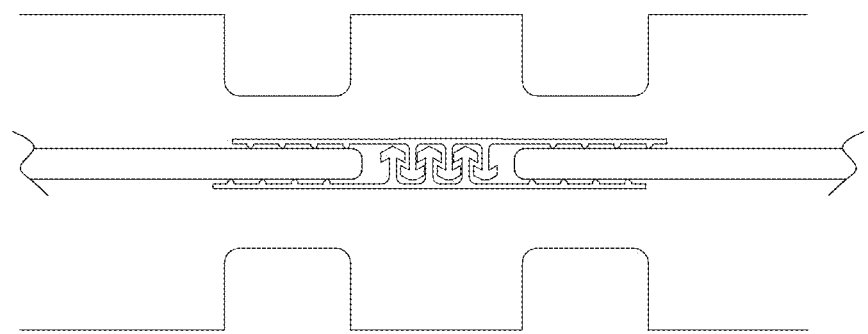
FIGS. 20B-20C illustrate example manufacturing methods of the zipper configuration of FIG. 20A.
Figure 20C:
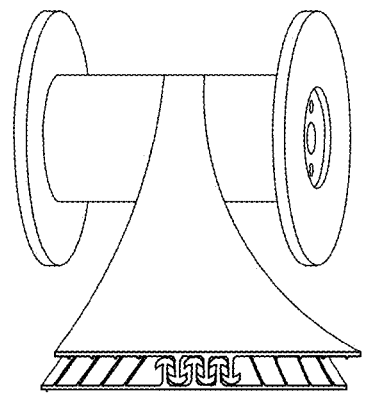
Figure 21A:
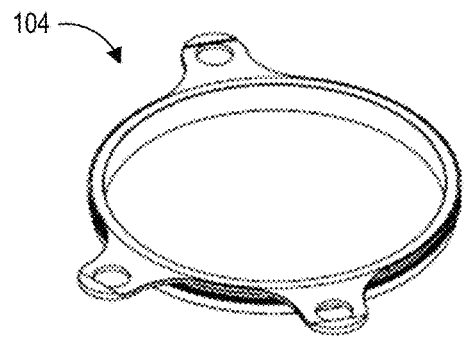
FIG. 21A illustrates an example bag coupling component of the bag of FIG. 1.
Figure 21B:
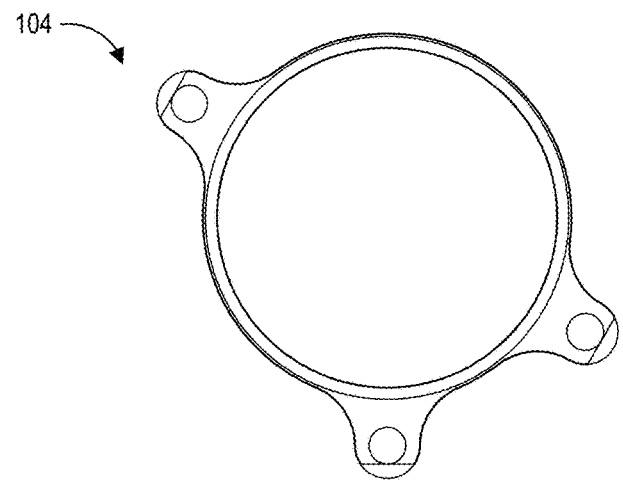
FIG. 21B illustrates a front view of the bag coupling component of FIG. 21A.
Figure 21C:
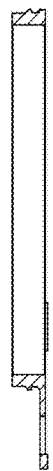
FIG. 21C illustrates a sectional view of the bag coupling component of FIG. 21B along axis A-A.
Figure 21D:
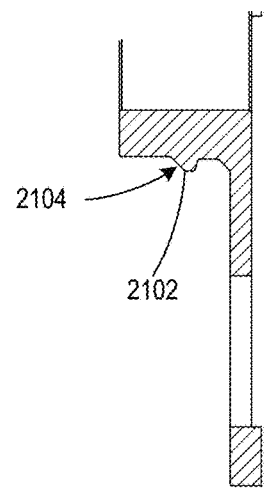
FIG. 21D illustrates a detailed view of the area B in the sectional view of FIG. 21C.
Figure 21E:
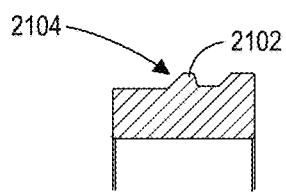
FIG. 21E illustrates a detailed view of the area C in the sectional view of FIG. 21C.
Figure 22A:
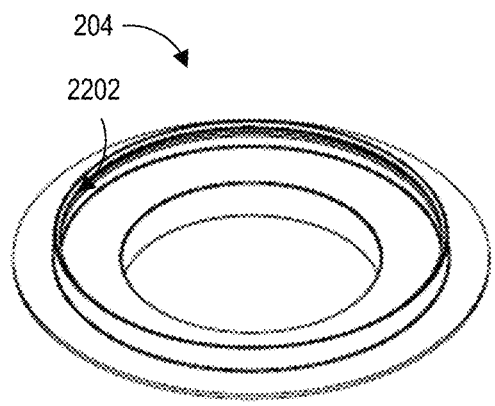
FIG. 22A illustrates an example wafer coupling component of the bag of FIG. 11C.
Figure 22C:
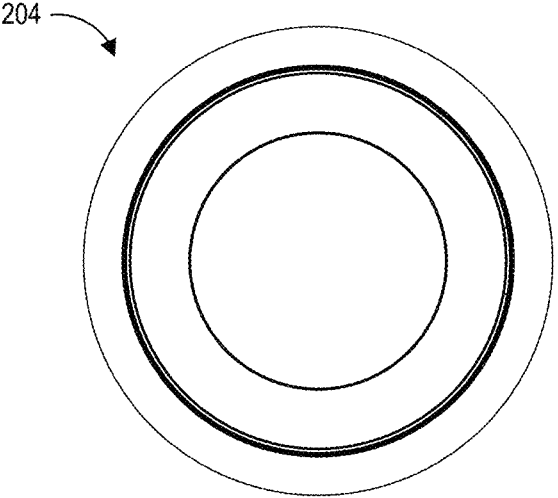
FIG. 22C illustrates a front view of the wafer coupling component of FIG. 22A.
Figure 22B:
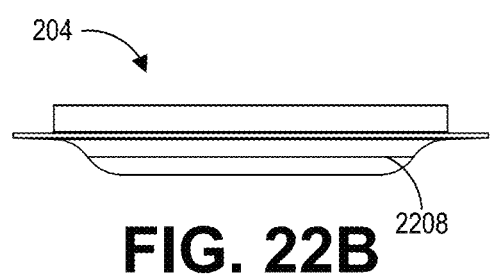
FIG. 22B illustrates a side view of the wafer coupling component of FIG. 22A.
Figure 22D:
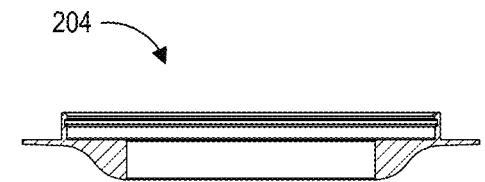
FIG. 22D illustrates a sectional view of the wafer coupling component of FIG. 22C along axis A-A.
Figure 22E:
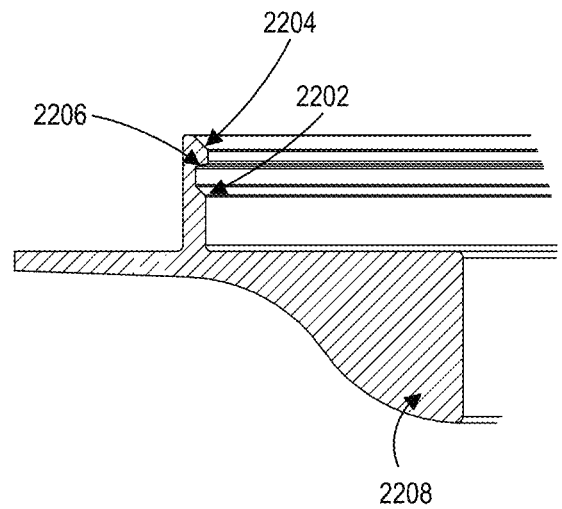
FIG. 22E illustrates a detailed view of the area C in the sectional view of FIG. 22D.

To close the bag 100, a user can first lift up the extension 117 of the sensor protector layer 116, which has the first seal 118 attached. The user can then roll or fold the extension 109 of the first and second bag films 108, 110 toward the front side of the bag 110 three times. The rolling can be guided by the three fold lines as shown in the detailed view of the extension 109 of the second bag film 110 in FIG. 3B. After the three rolls, the second seal 120 is now on the front side of the bag 100. The user can then lower the extension 117 of the sensor protector layer 116 so that the first and second seal 118, 120 can mate to releasably close the bag. The first and second seals 118, 120 can be two complementary zippers, such as shown in FIG. 20A. Although the zipper design in FIGS. 20A-20C show three rows, any other suitable numbers of rows, for example, six rows, can be used. The interlocking zipper of the first and second seals 118, 120 can create a fluid-tight seal. The user can form the seal by applying pressure to press the first and second seals 118, 120 toward each other. Any other suitable seal mechanism or fastener, such as Velcro connectors, clips, magnets, and the like, may be used as the first and second seals.

The bag 100 can include one or more drain detection sensors that can identify a drainage event of the bag 100. The bag sealing mechanism can include a metal strip 134 extending over the second seal 120 and the back tab 130 that is immediately adjacent the second seal 120. After having rolled the extensions 109 of the first and second bag films 108, 110 three times toward the front side of the bag 110, the metal strip 134 can contact one or more drain detection sensors 1804 (see FIGS. 5A-8B) on the sensor layer 112. The drain detection tabs 1804 can be made of any electrically conductive material, such as metal. Contact between the metal strip 134 and the drain detection sensors 1804 can complete a drain detection circuit, which is an open circuit before the bag 100 is used for the first time. In some examples, the drain detection circuit may complete, that is, the metal strip 134 may have a firm contact with the drain detection sensors 1804, only when the first and second seals 118, 120 are securely interlocked with each other.

The drain detection circuit can be in electrical communication with a hardware processor 1812 (see FIGS. 5A-9B), for example, a microprocessor, on the sensor layer 112. When the drain detection circuit is closed for the first time, the electronics of the bag 100 can be activated and the hardware processor 1812 can output an indication that the bag 100 is sealed and now in use. Upon being turned on, the hardware processor 1812 can transmit data to a remote server, which can record a time stamp of the bag in an activated status if the data packet is valid. An app on the user device can use the time stamped activated status to determine how many remaining bags are not in an activated status to determine remaining inventory. Any subsequent breaking of the drain detection circuit, and optionally also re-closing of the drain detection circuit after the drain detection circuit becomes open, detected by the hardware processor 1812 can be inferred as a drainage event. This is because the drain detection circuit can become open when a user opens the bag 100 to drain, resulting in the metal strip 134 no longer being in contact with the drain detection sensor(s) 1804. And when the user re-seals the bag 100 after draining the bag 100, the metal strip 134 can reestablish contact with the drain detection tab(s) 1804.

Using the drain detection circuit, the maintenance bag 100 can: (1) track the number of drain events that occur throughout the day and/or (2) provide inventory management to the user on the number of remaining bags in a medical kit. The hardware processor 1812 of the bag 100 can use machine learning to detect trends in the number of drains that a user typically has throughout the day. Based on these trends the bag 100 can alert the user, a healthcare professional, or a service team, when the user's drains have increased or decreased, for example, by a certain percentage or a predetermined threshold from their baseline. The bag 100 can send alerts by, for example, outputting a message to an app on the user device or to an email address. In addition, the ostomy system can detect when a bag has been discarded and a new bag activated. The hardware processor of the bag can wirelessly communicate with a remote server to send a message that a new ostomy bag has been activated. A processor on the remote server can decrease the number of new ostomy bags in a user's kit by one in response to the message. This new bag detection can provide inventory management within an app to alert the user when the user should order more products to avoid the possibility of running out of product before additional supplies arrive. The hardware processor 1812 or the remote server can either prompt the user to order more bags or automatically initiate an order of new bags.

The one or more drain detection sensors 1804 may be arranged at a lower portion of the bag sensor layer 112. FIGS. 5A-9B illustrate example configurations of a sensor layer of an ostomy bag. As illustrated in FIGS. 5A-8B, the one or more drain detection sensors 1804 may be arranged on a drain detection tab 1904 of the bag sensor layer 112. The drain detection tab 1904 can extend from a main body of the sensor layer 112 toward the bag opening side. The drain detection tab 1904 can have a shape and/or length suitable for maximizing a contact area with the metal strip 134 after the extensions 109 of the bag films 108, 110 have been folded three times toward the front side of the bag 100. As shown in FIGS. 5A-8B, the drain detection sensors 1804 can include two parallel strips extending along a length of the drain detection tab 1904. The drain detection tab 1904 may be configured to oriented differently, such as on a different layer with respect to the ostomy bag. In some examples, a drain detection tab 1904 may be included on a plurality of layers. As shown in FIGS. 5A-6B, the drain detection sensor 1804 may be on the drain detection tab

1904 on a front surface of the sensor layer 112. As shown in FIGS. 7A-7B, the drain detection sensor 1804 may be on the drain detection tab 1904 on a back surface of the sensor layer 112. As shown in FIGS. 8A-8B, the drain detection sensor 1804 may be on the drain detection tab 1904 on both the front and back surfaces of the sensor layer 112, and can be compatible with different variations of drain sensing or bag sealing mechanism configurations of the bag. In some examples, such as shown in FIGS. 9A-9B, the one or more drain detection sensors 1804 may be arranged on a main body of a sensor layer 912 closer to the bag opening side. The sensor layer 912 may not have a drain detection tab as shown in FIGS. 5A-8B.

Figure 10B:
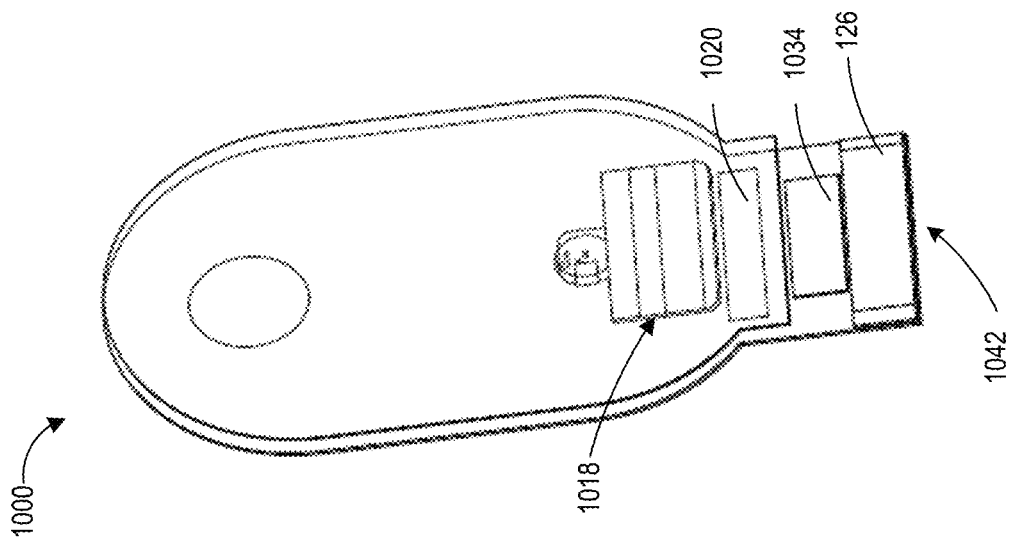
FIGS. 10A-10C illustrate back, perspective, and exploded views of another example ostomy bag without a printed circuit board (PCB).
Figure 10A:
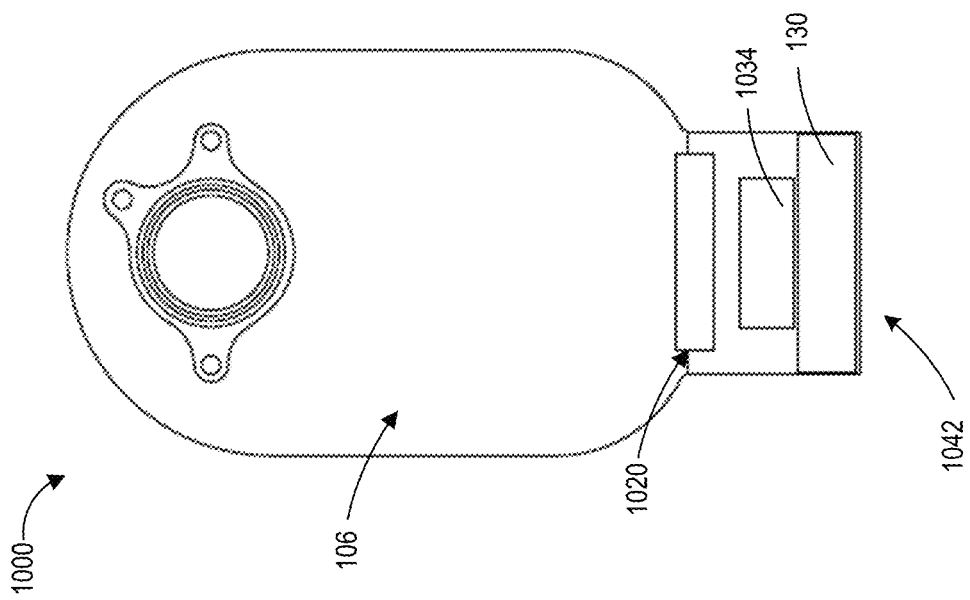
Figure 10C:
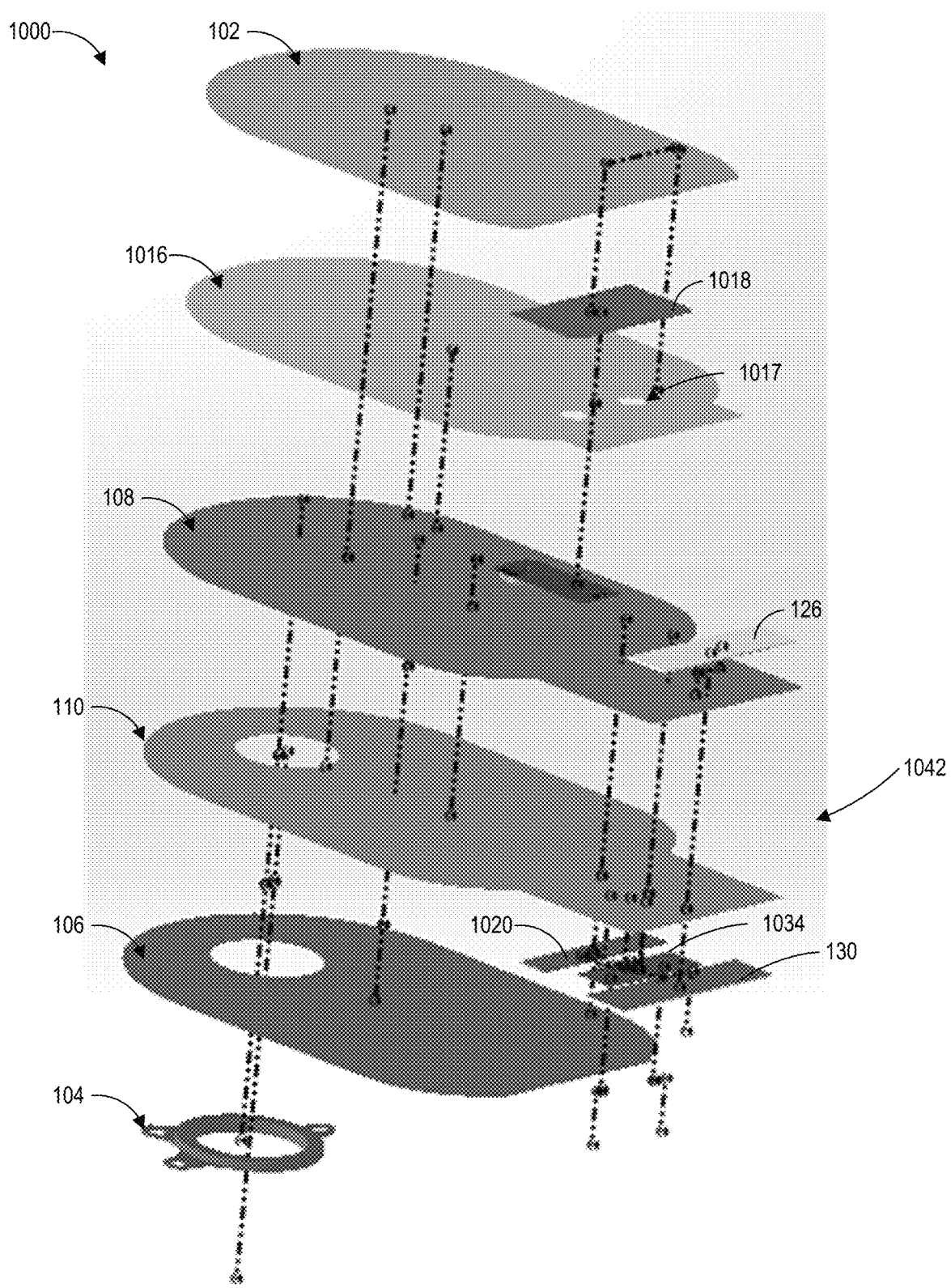

FIGS. 10A-10C illustrate another example ostomy bag 1000 with similar layers and a similar bag sealing mechanism as shown in FIG. 1-4, with the differences described with reference to FIGS. 10A-10C. The sensor layer in FIG. 10C is hidden from view for purposes of clarity. As shown in FIG. 10C, the sensor protector layer 1016 may not include an extension or tab. Rather, the sensor protector layer 1016 can include two openings 1917 toward the bag opening side 1042, or bottom side of the bag 1000. The openings 1017 can expose two drain detection electrodes 1804, such as shown in FIGS. 9A-9B. The first and second seals 1018, 1020 of the bag 1000 may but need not be zippers, and can alternatively be any releasable fastener disclosed herein. The metal strip 1034 of the bag 1000 may act as one of the second tabs. When the extension 109 of the bag films 108, 110 are rolled or folded three times toward the front side (the side facing away from the bag coupling component 104), the metal strip 1034 can contact the electrodes exposed by the openings 1017 of the sensor protector layer 1016 to complete a drain detection circuit.

The sensor layer of the bags disclosed herein can include anisotropic magneto-resistive (AMR) sensors, capacitive and/or thermistor sensors in addition to open circuit designs that can be closed when in contact with conductive material in order to detect drainage events. The bag sensor layer can include conductive tape in place of conductive traces for transmitting the information to the microprocessors. In some examples, the sensors can be located on more than one sensor layer. In addition to the drain detection tabs 1804, the bag sensor layer 112, 912 may further include, but are not limited to components such as electronics 1812 (which may include at least one hardware processor, such as a microprocessor, NFC antenna or Bluetooth component or other wireless communication hardware, accelerometer and/or other position/motion sensor 1422, and other electronic components), a battery 1406, a battery contact 1408, and one or more sensors 1806. The accelerometer and/or other position/motion sensor 1422 can detect a posture and/or orientation of the wafer and/or the posture and/or motion of the user, which can indicate whether the bag is upright, tilted, or lying generally flat. The electronics 1812 and the one or more sensors 1806 can be located on the back surface of the sensor layer 112. The battery 1406 can be located on the front surface of the sensor layer 1132. The battery 1406 can be a coin cell battery.

There may be no rigid PCB in the maintenance bags disclosed herein, such as the bags 100, 1000 illustrated in FIGS. 1-10C. Rather, the electronics 1812 including the microprocessors can be supported by the coin cell battery 1406. In an example, the coin cell battery 1406 can be cr2032 with a diameter of about 20 mm. Other types of coin cell batteries can also be used. The coin cell battery 1406 can be attached to the electronic 1812 and/or the sensor layer 112, 912 by electrically conductive adhesive. At least a portion of the electronics 1812 can be located closer to a center of the coin cell battery 1406 to reduce components detaching during flexing of the bag. In some examples, the bag sensor layer may have a flexible or rigid material or board. Electrical components may be directly or indirectly coupled to the board or flexible material. The one or more sensors 1806 can be oriented such that the sensors 1806 can be parallel or substantially parallel to the bag bending line, thereby reducing breaking of the sensors 1806. The sensor layer 112 may be flexible enough such that openings in the sensor layer to improve flexibility may no longer be necessary, such as shown in FIGS. 5A-5B, 6A-6B, and 8A-8B. In some examples, the sensor layer 112 may still include a plurality of openings 1802, such as shown in FIGS. 7A-7B and 9A-9B to improve flexibility of the sensor layer 112, 912.

In some examples, the battery 1406 may be coupled to the sensor layer with solder tabs. In some examples, the battery 1406 may be coupled to the sensor layer with electrically conductive adhesive in addition or in the alternative to solder tabs. The battery contact 1408 may be a tab that can fold over the battery 1406. The tab 1408 may complete an electrical connection with the battery 1406 and electronic components of the layer and/or other components of the ostomy bag or wafer when folded over to be in contact with the battery 1406.

The one or more sensors 1806 may include anisotropic magneto-resistive (AMR) sensors, capacitive and/or thermistor sensors. In some examples, the one or more sensors 1806 are all thermistors. In some examples, the sensor layer may include 42 thermistors, 48 thermistors, or a different number of thermistors. The plurality of thermistors 1806 may be configured in an array across a surface of the sensor layer. The thermistors 1806 can be used to determine the bag fill level as the temperature of the effluent can be substantially the same as the human body temperature, which is assumed to be greater than the temperature of the bag attach to the body of the user. The array of thermistors 1806 can allow for bag fill detection even when the bag is tilted at an angle rather than being upright. The thermistors 1806 may be oriented horizontally, vertically, or at an angle with a longitudinal axis of the layer or bag. In some examples, the thermistors may be angled 90 degrees with respect to a longitudinal axis of the layer or bag or angled parallel with the bag bending line, which may, in some examples, be at a 90 degree angle with respect to the longitudinal axis of the layer or bag. Advantageously, this angle of the thermistors 1806 may reduce breakage due to bending of the thermistors. Some or all of the electrical connections, such as trace, between sensors and the electronics 1812 may be reinforced or thickened so as to reduce the risk of breakage during use. In some examples, the trace may have a thickness be between 3 and 4 mm or greater or less than that range, such as 2 mm, 3 mm, or 4 mm.

A wafer can be used with the maintenance bags disclosed herein. The wafer can be coupled to the skin of a user so as to couple the bag to the user. As will be described below, the wafer can include one or more of features including but not limited to:

- A top film layer with improved user comfort.
- Better coupling design for easier attachment and overall better security.
- A larger coupling allowing for accommodation of larger stoma sizes.
- A hydrocolloid formula providing greater comfort and strong seal for even longer wear-times than existing hydrocolloid adhesives.

Skin temperature monitoring and leaks detection.

Inventory tracking.

Figure 11B:
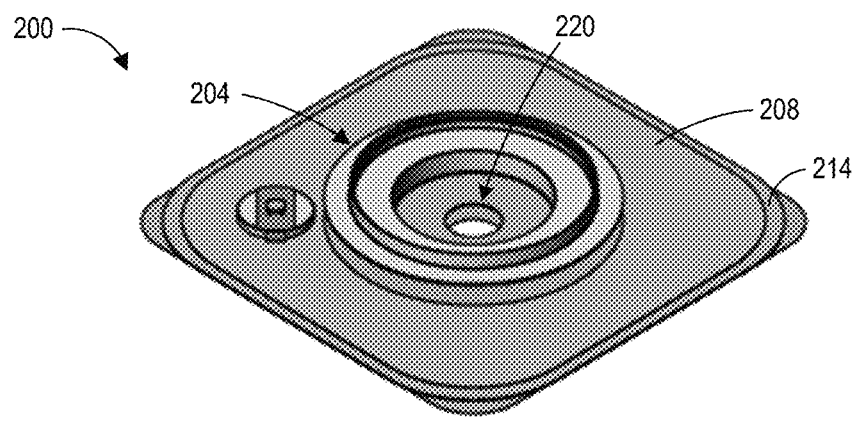
FIG. 11B illustrates a perspective view of the example wafer of FIG. 11A.
Figure 11C:
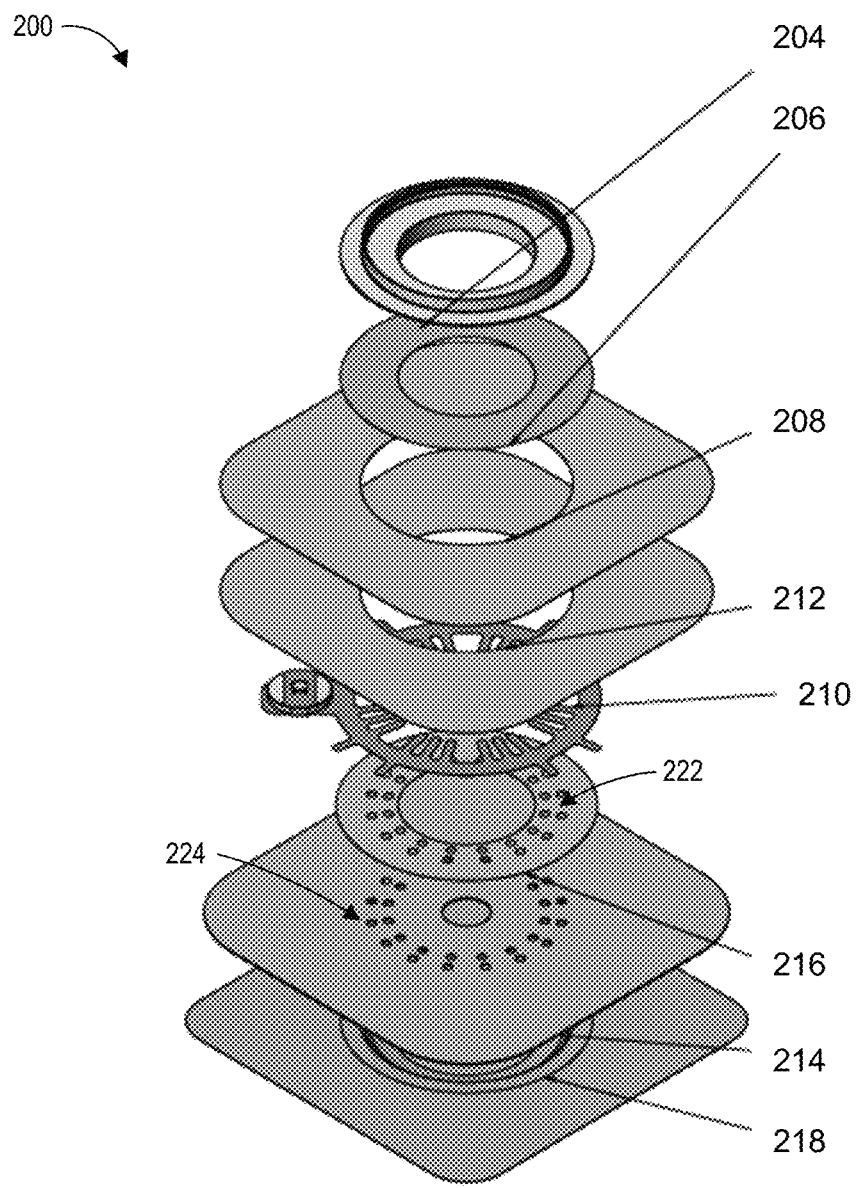
FIG. 11C illustrates an exploded view of the example wafer of FIG. 11A.

FIGS. 11A-11C illustrate an example wafer 200. The wafer 200 can have a front side that faces away from the user. The front side can terminate at a wafer coupling component 204. The wafer coupling component 204 can releasably mate with the bag coupling component 104 described above. As shown in FIGS. 21A-21E, the bag coupling component 104 can include a circumferential ridge 2102 around an outer wall of the bag coupling component 104. The circumferential ridge 2102 can include a chamfer 2104 on the back side, that is, the side facing the user during use. As shown in FIGS. 22A-22E, the wafer coupling component 204 can include a corresponding groove 2202 around an inner wall of the wafer coupling component 204. The wafer coupling component 204 can include a chamfer 2204 toward the front side on the inner wall. The inner wall of the wafer coupling component 204 has a greater diameter than the outer wall of the bag coupling component 104. When the bag coupling component 104 moves toward the wafer coupling component 204, the chamfer 2204 on the inner wall of the wafer coupling component 204 and the chamfer 2104 on the circumferential ridge 2102 of the bag coupling component 104 can guide the sliding of the bag coupling component 104 onto the wafer coupling component 204 until the ridge 2102 securely engages the groove 2202. The groove 2202 also includes a chamfer 2206 on the front side to guide the disengagement of the ridge 2102 from the groove 2202 when the bag coupling component 104 is moved away from the wafer coupling component 204. The coupling mechanism disclosed herein can accommodate relatively large stomas, for example, in the range of between about 20 mm to about 54 mm. The coupling mechanism disclosed herein can reduce the force required to couple the bag and wafer together, while maintaining a seal strong enough to prevent leakage. The coupling mechanism can require no greater than or about 0.85 psi (about 5.86 kPa) to seal and greater than or about 2.5 psi (about 17.2 kPa) to decouple. The coupling mechanism can optionally provide for a positive clicking sound when the bag and wafer coupling components are properly secured together.

The wafer coupling component 204 can be attached to a top film layer 208 by a coupling adhesive layer 206 on a front surface of the top film layer 208. On the back surface of the top film layer 208, a wafer sensor layer 210 can be attached to the top film layer 208 by a top film adhesive layer 212. On a back surface of the wafer sensor layer 210, the wafer sensor layer 210 can be attached to a user adhesive layer 214 by a sensor adhesive layer 216. The user adhesive layer 214 can include hydrocolloid. Before the wafer 200 is used, the back side, that is, the user-facing side of the user adhesive layer 214 can be protected by a release liner 218.

FIGS. 12A-17C illustrate back and front views of example wafer sensor layers 210. The wafer sensor layer 210 can include an interface 1412 that can include on the back surface of the interface 1412 a plurality of electronics, for example, at least one hardware processor, such as a microprocessor, NFC antenna or Bluetooth component or other wireless communication hardware, accelerometer and/or other position/motion sensor, and other electronic components. In some examples, the electronics may further include a button or other touch sensitive device. The button may allow for certain functionality, such as a press or touch for wakeup. Upon being turned on, the wafer can transmit data to a remote server, which can record a time stamp of the wafer in an activated status if the data packet is valid. The app on the user device as described above can use the time stamped activated status to determine how many remaining wafer are not in an activated status to determine remaining inventory. The interface 1412 can include a portion on the front surface of the interface 1412 that can be coupled to a battery 1406. In some examples, the battery 1406 may make an electrical connection to the electronics on the interface 1412. In some examples, a first battery terminal may connect to the electronics at manufacture. The first terminal connection may be permanent, semi-permanent, or temporary. In some examples, the interface 1412 may include a tab 1408 that can make an electrical connection to the battery 1406. For example, the tab 1408 may include an electrical contact such that a circuit is formed when the electric contact comes into contact with the battery 1406. In some examples, the electrical contact may be on a front surface of the tab 1408. As shown in FIGS. 16C and 17C, when the tab 1408 is folded such that the front surface comes in contact with the battery 1406, one or more electronic components of the interface 1412 or other related components may be powered by the battery 1406. The tab 1408 may be flexible or have a flexible portion so as to allow the tab to fold in order to facilitate contact between the electrical contact on the front surface of the tab 1408 with an electrical contact of the battery 1406. In some examples, the electrical contact of the tab 1408 may make an electrical connection with the battery 1406 only after a threshold pressure is applied to the tab 1408 or battery 1406.

Size of the wafer sensor layer 210 may be between 40 and 70 mm or greater or less than that range. In some examples, a size of the wafer sensor layer 210 may be 57 mm. The thickness of the conductive traces and/or the spacing between the conductive traces can be varies, such as shown in FIGS. 12A-17C and can be similar to the thickness of conductive traces of the bag sensor layer disclosed herein.

Figure 12A:
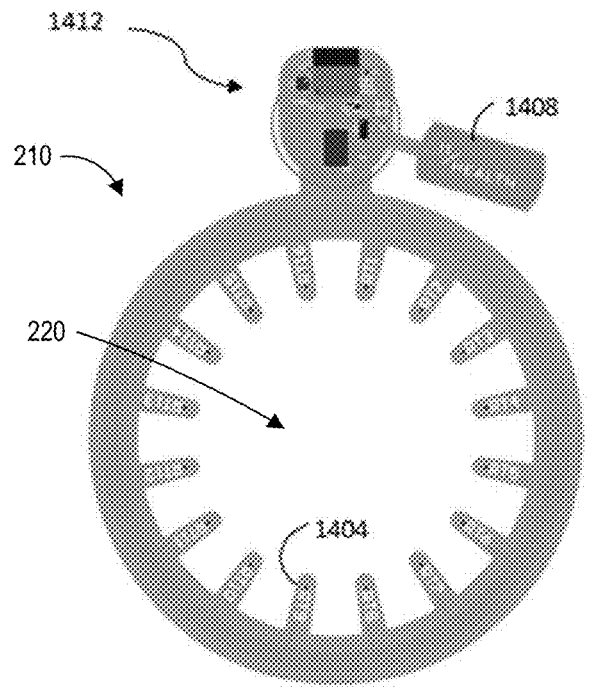
Figure 12B:
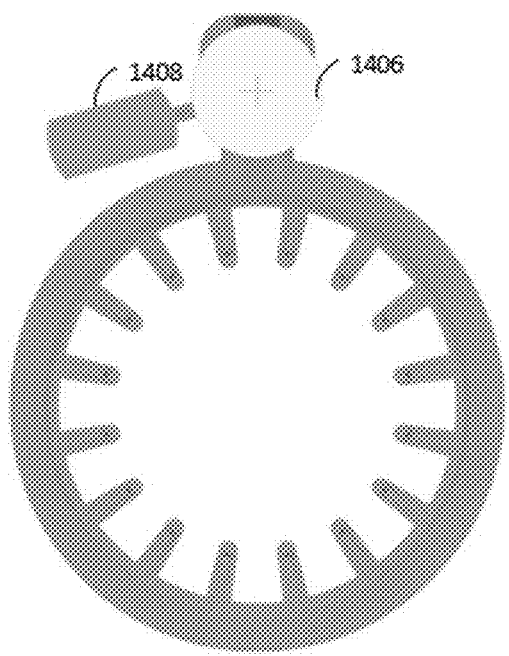

In the illustrated examples, the wafer sensor layer 210 can include a plurality of temperature sensors 1407. The temperature sensors 1407 may be thermistors. The temperature sensors 1407 can be located on the back surface, that is, the user-facing surface of the wafer sensor layer 210. The plurality of temperature sensors 1407 can be configured to measure temperature of the skin of the patient. In some examples, the plurality of temperature sensors 1407 may be configured in an inner ring configuration around a central stoma opening 220. As illustrated, the plurality of temperature sensors 1407 may be configured to couple to or be embedded in fingers or protrusions 1404 on the wafer sensor layer 210. The fingers or protrusions 1404 may extend towards the central opening 220. The fingers 1404 can have substantially the same length. Each finger or protrusion 1404 (for example, as shown in FIGS. 12A-12B) or a subset of the fingers or protrusions 1404 (for example, as shown in FIGS. 13A-17C) may have an associated temperature sensor. The temperature sensors 1407 can be located at generally the same distance from a tip of the fingers 1404. The number and/or distribution of the temperature sensors 1407 can allow thermographic mapping of the skin temperature of the user's skin under the wafer. The thermographic mapping can allow detection of inflammation (with greater details provided further below), including but not limited to existing localized inflammation and/or a potential risk of inflammation. This is because local elevation in skin temperature may be associated with wound and/or periwound infection and/or inflammation, including but not limited to skin inflammation and deep inflammation. Other configurations of fingers or protrusions 1404 and/or temperature sensors are also possible. Advantageously, the configuration of fingers 1404 in a ring formation may facilitate better fit around a stoma of a user and allow for better monitoring of conditions around the stoma while reducing the size or surface area of the sensor layer, which can improve flexibility of the wafer 200 and better fit with the user's skin surface.

A spacing between inner finger 1404 may be uniform or non-uniform, symmetric or asymmetric, or in another configuration. A sensor may be included on each finger 1404 or a subset of fingers 1404. Different sensors may be included on different fingers 1404. More than one sensor may be included on each finger 1404. Some fingers 1404 may include a plurality of sensors and some fingers 1404 may include one or no sensors.

The inner ring of the wafer sensor layer 210 may include 8, 16, 24, 32 or more or fewer fingers 1404. FIGS. 12A-12B illustrate back and front views of an example layer with 16 fingers 1404. FIGS. 13A-17B illustrate back and front views of an example layer with 32 fingers 1404. The spacing between the fingers 1404 can be uniform such as shown in FIGS. 12A-13B, or non-uniform as shown in FIGS. 14A-17C.

Figure 13A:
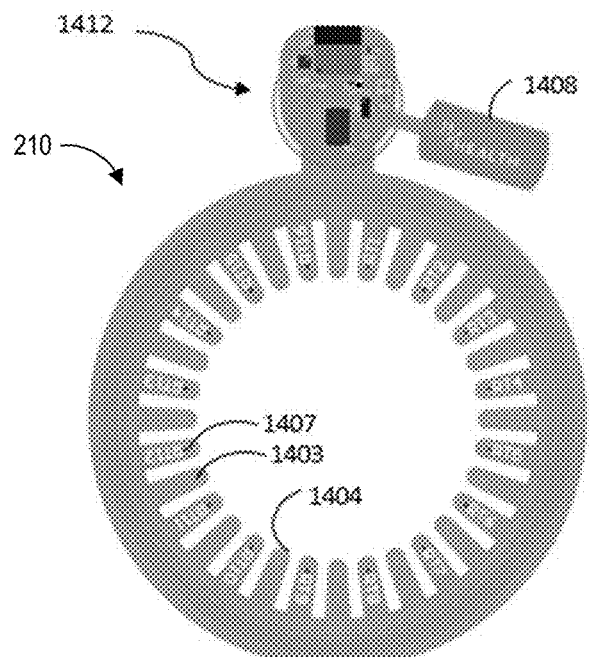
Figure 13B:
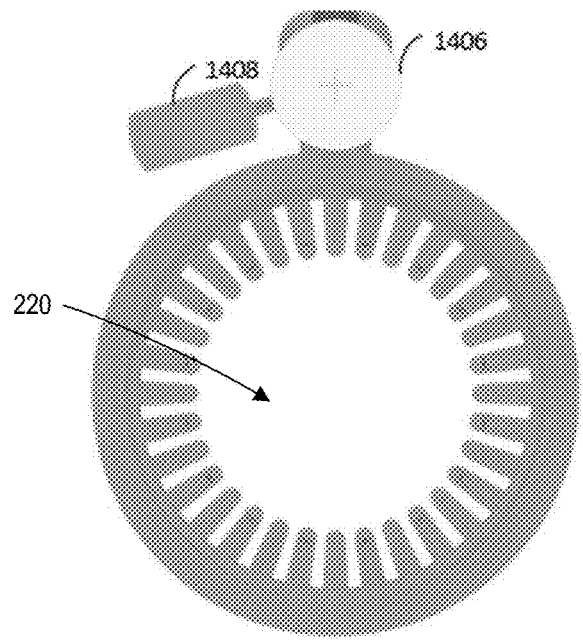
Figure 16A:
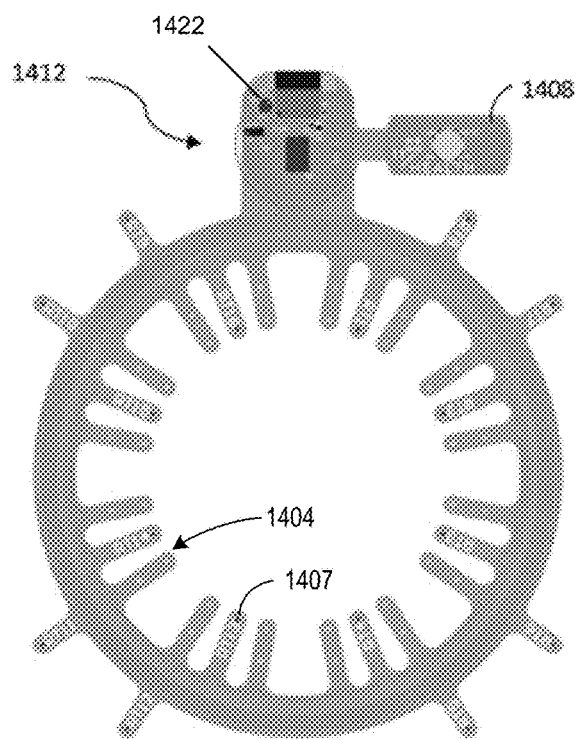
Figure 16B:
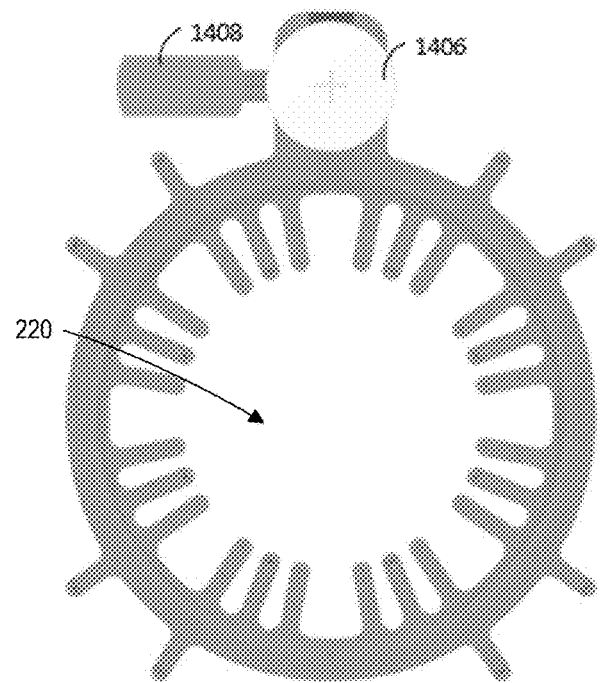
Figure 16C:
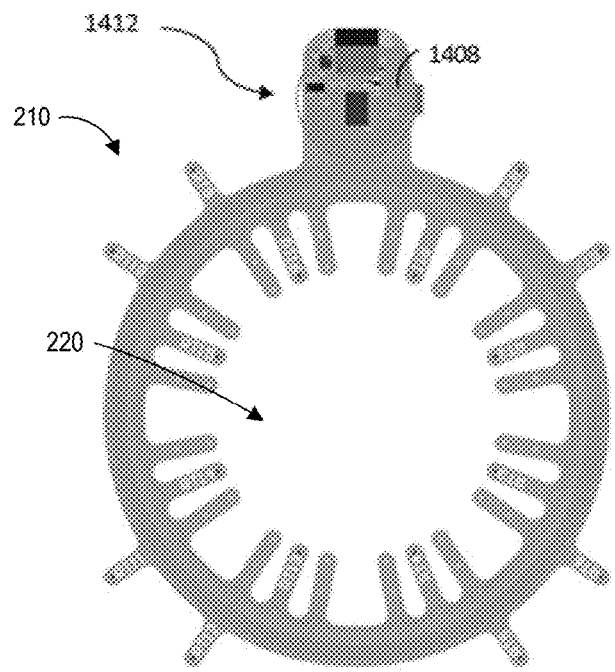

The wafer sensor layer may additionally or alternatively include other sensors coupled to or embedded in the fingers or provided elsewhere on the layer. For example, as illustrated in FIGS. 13A-17C, a subset of the fingers 1404 may include temperature sensors 1407 and a subset of fingers may include leak sensors 1403. In FIGS. 13A-13B, the fingers 1404 can each alternatingly including a temperature sensor 1407 and a leak sensor 1403. As shown in FIGS. 14A-17C, each finger 1404 that includes a temperature sensor 1407 can be accompanied by fingers including leak sensors 1403 on both longitudinal sides of the finger 1404 including the temperature sensor 1407. The three fingers 1404 can form one sensing region. The spacing between the sensing regions can be greater than the spacing between the fingers 1404 within the same sensing region.

In some examples, the wafer sensor layer 210 may include a plurality of fingers 1402 on an outer ring side of the interface. FIGS. 14A-17C illustrate back and front views of example wafer sensor layers 210 including a plurality of radially outwardly extending fingers 1402 on an outer ring. The fingers 1402 can have generally the same length. The fingers 1402 may be symmetrically or asymmetrically spaced around the wafer sensor layer 210. In the illustrated example, two or more fingers 1402 may be spaced closer together to form a finger pair. Spacing between the finger pairs can be greater than the spacing between the two fingers 1402 of the same pair. For example, a wafer sensor layer may include 8, 16, or more or fewer fingers 1402. In the illustrated example of 8 fingers 1402 (FIGS. 14A-17C), a distance between a first and second finger 1402 of the same pair may be approximately one half, one third, or more or less of a fraction of the distance between a second finger 1402 and a third finger 1402 that belong to different pairs. The wafer sensor layer 210 may include four finger pairs, one in each quadrant such as shown in FIG. 15B. The outer fingers 1402 may include a plurality of temperature sensors 1407, such as thermistors. The temperature sensors 1407 can be located at generally the same distance from a tip of the fingers 1402. In the illustrated example, a single thermistor 1407 is coupled to each outer finger 1402. Advantageously, the outer 8 thermistors on the fingers 1402 may allow detection of portions of the wafer 200 peeling off from the body of the user. Additionally or alternatively, the outer fingers 1402 may include different sensors.

As described above, a subset of the inner fingers may include a plurality of temperature sensors 1407. For example, 8 inner fingers 1404 may include a plurality of temperature sensors 1407. In some examples, temperature sensors 1407 in the inner ring may be angularly offset in polar coordinates from temperature sensors 1407 in an outer ring on outer fingers 1402. The polar coordinate frame may have a center at the center 1401 of the ring portion of the wafer sensor layer 210. Alternatively, the temperature sensors 1407 in the inner ring (that is, on the inner fingers 1404) may align with the temperature sensors 1407 in the outer ring (that is, on the outer fingers 1402) in polar coordinates.

The wafers disclosed herein can optionally include openings, for example, a plurality of microfluidic channels, in the hydrocolloid layer that would allow the effluent to be directed onto the temperature sensors. As shown in FIG. 11C, all the layers of the wafer 200 can include a central stoma opening 220. In addition, the sensor adhesive layer 216 and the user adhesive layer 214 can each include a plurality of smaller openings 222, 224 surrounding the central stoma opening 220. The plurality of smaller openings 222, 224 can form one or more rings (for example, concentric rings) around the central stoma opening 220. Within each ring, the plurality of smaller openings 222, 224 can be generally evenly spaced apart. The plurality of smaller openings 222 on the sensor adhesive layer 216 and the plurality of smaller openings 224 on the user adhesive layer 214 can substantially overlap with one another when the wafer is assembled. The plurality of smaller openings 222 on the sensor adhesive layer 216 and the plurality of smaller openings 224 on the user adhesive layer 214 can substantially overlap with the leak sensors 1403 when the wafer is assembled. The overlap of the smaller openings 222, 224 and the leaks sensors 1403 allow any moisture or fluid on the user's skin underneath the user adhesive layer 214 to directly reach and contact the exposed leak sensors 1403 on the bottom surface of the wafer sensor layer 210. In addition to the presence of the smaller openings, a non-woven fabric layer may be placed between the user adhesive layer and the sensor layer. The fabric can act as a wicking material to disperse the effluent to the temperature sensors, which can provide for a more instantaneous recording of temperature changes. The temperature changes can also demonstrate the presence of a leakage occurring. Alternatively, the dispersion of the effluent to the temperature sensors may short the temperature sensors, which can provide an indication of leak. Additionally or alternatively, the leak sensors of the wafers disclosed herein can include open circuit designs that can be closed when in contact with effluent in order to detect leakage. The openings in the user adhesive or hydrocolloid layer may allow the effluent to reach a plurality of leak sensors (for example, electrodes or conductors) that are in an open circuit design to close the circuit. In addition, the wafers disclosed herein can include an open circuit design may optionally include a non-woven fabric layer to direct the effluent to the conductors in order to more accurately detect the occurrence of a leakage. More details of leak detection using the open circuit design will be described below with reference to FIGS. 13A-18B.

In some examples such as shown in FIGS. 13A-18B, one or more sensors on the wafer sensor layer 210 may include leak sensors 1403. Leak sensors may be configured to detect moisture or other indicator of a leak from or near a stoma of a user. The leak sensors 1403 may be spaced so as to allow for a determination of approximate location of a leak. For example, the leak sensors 1403 may be spaced apart so that a leak is less likely to activate nearby sensors. The size and shape of the leak sensors can vary. The distance between the leak sensors can vary. In FIGS. 13A-14B, the leak sensors 1403 can each include two electrodes adjacent to each other.

In the illustrated examples, each electrode can be generally a half circle. The spacing between the two half circles in FIGS. 13A-13B can be smaller than the spacing between the two half circles in FIGS. 14A-14B. In FIGS. 15A-17C, the leak sensors 1403 can each include two circular electrodes spaced apart along a length of the finger 1404. The leak sensors 1403 can be located at generally the same distance from a tip of the fingers 1404, and therefore also generally the same distance from a center of the opening 220.

In some examples, the leak sensors 1403 may be oriented within a ring of the wafer sensor layer 210 to be separated or clustered into sections or quadrants. For example, a plurality of leak sensors 1403 may be separated or split into 4 quadrants (1411A, 1411B, 1411C, 1411D as illustrated in FIG. 15B) in a polar coordinate frame of the ring, wherein a center of the coordinate frame is located at the center 1401 of the ring portion of the wafer sensor layer 210. For example, the placement of the leak sensors 1403 in the different quadrants 1411A, 1411B, 1411C, 1411D may allow a system to determine a direction that a leak has occurred when an orientation of the device is known. The orientation of the device may be determined based on data from an inertial measurement unit (such as a gyroscope and/or accelerometer), which may be located at the interface 1412 as described above. Alternatively or additionally, an individual leak sensor 1403 can be configured to detect the precise location of a leak within a quadrant depending upon the presence of additional processor modules. The inclusion of additional processor modules would allow for the leak sensors to detect, for example, when a potential leak is becoming larger, as effluent spreads to additional leak sensors within a quadrant or to a different quadrant. Additional details of leak detection algorithms will be described further below.

Figure 18A:
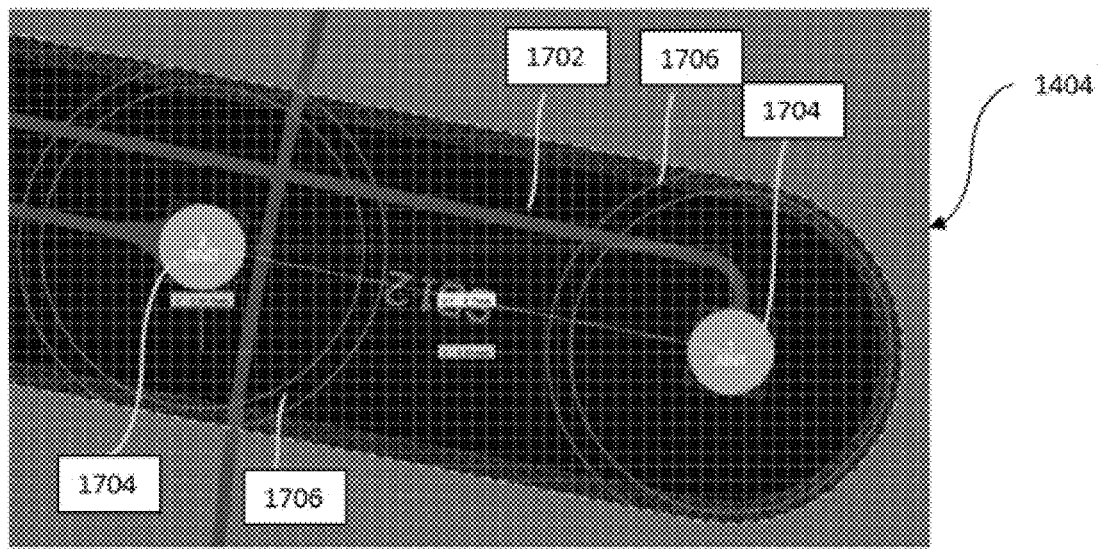
FIGS. 18A-18B illustrate various configurations of example leak sensors of a wafer of the present disclosure.
Figure 18B:
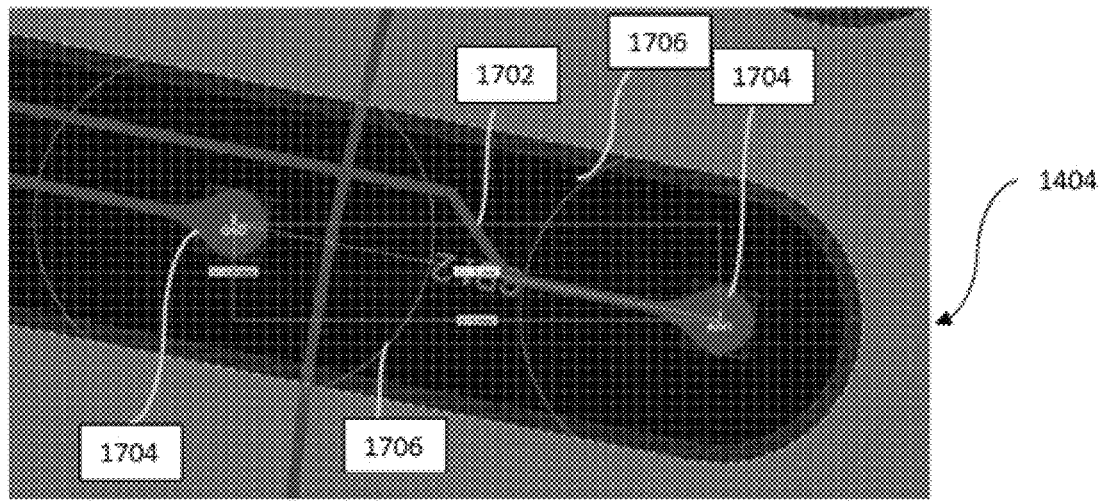

FIGS. 18A-18B illustrate example orientation of example leak sensors that may be part of the wafer sensor layer 210, such as on a finger 1404 as shown in FIGS. 15A-17C. The leak sensors may be split up into 4 or more or fewer quadrants, facilitating the determination of where the leak occurred. The leak sensors may also allow for determination of the location of the leak based on the location of the individual leak sensors that has been contacted by effluent. The size of the smaller openings 224 on the user adhesive layer 214 may be bigger than the exposed leak sensor 1403 since the hydrocolloid saturates and expands due to moisture and sweat, which can cause the smaller opening 224 of the hydrocolloid layer to close up and cover up exposed leak sensor 1403.

As shown in FIGS. 18A-18B, the leak sensor may include contacts or electrodes 1704 configured to generate an electrical signal when in contact with moisture. In some examples, such as illustrated in FIGS. 18A-18B, the contacts or electrodes 1704 may be round. Other shapes may also be possible, such as semi-circular or tear drop shaped, such as illustrated in FIGS. 13A-14B and 18B. A distance between points on the contacts (such as a center of each contact) may be, for example, 4 mm or greater or less, such as 4.7 mm as shown in FIG. 18A or 5.2 mm as shown in FIG. 18B. In the illustrated examples, the contact 1704 closer to the base of the finger 1404 can be the ground electrode. Alternatively, the contact 1704 closer to the tip of the finger 1404 can be the ground electrode. The wafer may include one or more smaller openings 1706 on the user adhesive layer. In some examples, the wafer may include a single smaller opening on the user adhesive layer. In some example examples, the wafer may include a plurality of smaller openings on the user adhesive layer, such as 2 or more. The smaller opening on the user adhesive layer may be circular, such as illustrated in FIG. 18A or an extended circle, an oblong shape, or other shape, such as illustrated in FIG. 18B. The smaller opening on the user adhesive layer may be between 1.4 mm and 1.6 mm in radius or have a radius greater or less than that range. In some examples, such as where the smaller opening on the user adhesive layer is an elongated circle, the opening size can be about 1.75 mm in radius and extended by about 0.7 mm in a single direction. An electrical connection 1702 to the electrodes or contacts 1704 may be tear shaped such as illustrated in FIG. 18B, in some examples. This may advantageously reduce the potential for tearing during use of the wafer.

The detection of moisture by the leak sensor may be due to voltage change detected between the two electrodes. The voltage can change based on the amount of effluent present between the electrodes. The rate of change of voltage can be indicative of whether it is a leak or the presence of sweat. The leak sensors can output signals to the hardware controller on the wafer sensor layer. When the leak sensors are divided into four quadrants as described above, each quadrant may output a single leak sensor value, which can be an analog-to-digital conversion value. The sensors in each quadrant can be sampled at a predetermined rate, for example, between 1 sample/minute to 10 samples/minute. Alternatively, each leak sensor can output a single leak sensor value, or the two leak sensors of each sensing region (that is, the three-finger configuration with a temperature sensor between two leak sensors as described above) can output a single leak sensor value. The hardware controller can also sample the battery voltage at a predetermined rate, preferably the same sampling rate as the leak sensors. The single leak sensor value can be normalized by the battery voltage to get a normalized sample value of between 0 to 1.0 can indicate a complete short signaling a leak. 1 can indicate a complete open showing no leak. Normalizing the leak value by the battery value can improve the accuracy of leak detection. The hardware controller can average the normalized sample value using a symmetric sliding window of a predetermined one-sided size, to obtain a windowed mean, for example, for each quadrant, or each leak sensor, or each sensing region. The hardware controller can then calculate the slope of the windowed mean, for example, for each quadrant, or each leak sensor, or each sensing region, using the Thiel-Sen slope estimator. The hardware controller can monitor one or more of a plurality of values calculated from the leak sensor readings, for example, the calculated slope value and the windowed mean value, and output alerts accordingly to, for example, a user device such as a smartphone or the like.

Some non-limiting examples of leak monitoring based on the leak sensor readings will be described. If the slope stays below a first threshold continuously for longer than a first time period, for example, between 5 minutes to 30 minutes, the hardware controller can output a first alert, which can be a rapid moisture content change alert. This may indicate that a leak has just occurred, for example, for that quadrant, or that leak sensor, or that sensing region. If the windowed mean stays below a second threshold continuously for longer than a second time period, for example, between 20 minutes to 2 hours, the hardware controller can output a second alert, which can be a persistent moisture alert, for example, for that quadrant, or that leak sensor, or that sensing region. If the windowed mean stays below a third threshold continuously for longer than a third time period, for example, between 1 minute and 30 minutes, the hardware controller can output a third alert, which can be a high moisture alert, for example, for that quadrant, or that leak sensor, or that sensing region. The third threshold may be lower than the second threshold. If the windowed mean stays below a fourth threshold continuously for longer than a further time period, for example, between 5 minutes and 1.5 hours, the hardware controller can output a fourth alert, which can be a potential leak alert, for example, for that quadrant, or that leak sensor, or that sensing region. The fourth threshold may the same, higher, or lower than the third threshold. The hardware controller may output a final determination of a leak when thresholds for one or more of the above-described alerts have been met. For example, the hardware controller may determine that there is an effluent leak when thresholds for the third and/or fourth alerts have been met. The hardware controller may only display an alert on the user device the final determination of a leak.

Additionally, the hardware controller can output inflammation detection based on signals from the thermistors in each quadrant. In an example, the hardware controller can output a detection of localized inflammation in response to detecting a temperature growth of greater than between about 1° C. to about 2.5° C., or between about 1.5° C. to about 2° C. in a quadrant. In another example, the hardware controller can determine that the user is likely having a fever in response to detecting a temperature growth across all four quadrants. The inflammation detection process of the hardware controller may not require information of temperature of the user at a different location as a reference temperature. The hardware controller can sample the thermistors, for example, 4 thermistors in the illustrated examples of FIGS. 12A-17C, in each quadrant at a predetermined sampling rate. The sampling rate can vary, for example, at about 1 sample/minute to 5 samples/minute or more. The hardware controller can determine a quadrant temperature value by taking the mean of all the thermistor readings in that quadrant. The hardware controller can process the quadrant temperature, for example, by smoothing and/or down-sampling, which can be achieved by combining a certain number of samples and taking their mean. The hardware controller can further smooth the processed quadrant temperature using a symmetric sliding window of a predetermined one-sided size for further noise suppression. The further smoothed quadrant temperature is a short-term mean for that quadrant. The hardware controller can calculate a long-term mean for that quadrant by combining the short-term mean values for that quadrant within a certain time period (for example, 5 minutes, 10 minutes, 15 minutes, 20 minutes, 25 minutes, 30 minutes, or otherwise). The hardware controller can calculate a difference between the short-term and long-term means for each quadrant and further calculate the slope of the difference using the Thiel-Sen slope estimator. The hardware controller can monitor one or more of a plurality of values calculated from the temperature sensor readings, for example, the calculated slope value, difference value, and the other calculated values, and output alerts accordingly to, for example, a user device such as a smartphone or the like. The high temperature alerts can be indicative of inflammation at that quadrant.

Some non-limiting examples of inflammation monitoring based on the temperature sensor readings will be described. If the slope exceeds a first threshold and the difference is higher than a predefined fraction of the long-term mean continuously for a first time period (for example, 20 minutes, 40 minutes, 1 hour, 1.5 hours, 2 hours, etc.), the hardware processor can output a first alert, which can be a high quadrant temperature growth alert. If the difference grows monotonically, that is, the slope is greater than or equal to zero, and the difference is higher than a predefined fraction of the long-term mean continuously for a second time period (for example, 30 minutes, 1 hour, 2 hours, 3 hours, 4 hours, 5 hours, 6 hours, 7 hours, 8 hours, etc.), the hardware processor can output a second alert, which can be a persistent quadrant temperature growth alert. If the short-term mean for that quadrant is greater than a certain temperature value continuously for more than a third time period (for example, 20 minutes, 40 minutes, 1 hour, 1.5 hours, 2 hours, etc.), the hardware processor can output a third alert, which can be a high quadrant temperature alert. If the difference is greater than a predefined temperature difference value continuously for more than a fourth time period (for example, 20 minutes, 40 minutes, 1 hour, 1.5 hours, 2 hours, etc.), the hardware processor can output a fourth alert, which can be a high quadrant temperature-difference alert. The hardware controller may output a final determination of inflammation when thresholds for one or more of the above-described alerts have been met. The hardware controller may only display an alert on the user device the final determination of inflammation.

As described above, a position and/or orientation sensor 1422, for example, an accelerometer, can provide additional information that can be combined with the leak and/or temperature sensor data for leak and/or inflammation detection. The accelerometer can measure the orientation of the wafer, defined as the angle at which the wafer accelerometer is rotated relative to the user's body. This measurement can be used to identify the wafer quadrants and help localize the inflammation/leakage area that the respective detection methods disclosed herein identify as potentially at risk of a leak and/or inflammation.

The accelerometer measurements can be sampled at a predetermined rate, for example, at a similar sampling rate as that of the leak sensor and/or temperature sensor. Each accelerometer measurement is the acceleration $a=(a_x; a_y; a_z)$ in the Cartesian coordinates of an accelerometer frame. The accelerometer on the wafer can be assumed to be pointing in the y direction, which is perpendicular to the vertical, that is, the direction of the gravitational acceleration. A rotation angle that contains the orientation information can be obtained from the values of $a_x$ and $a_y$. An angle of inclination of the accelerometer frame with the vertical can be calculated using the values of $a_z$ and the magnitude of the acceleration a. The data calculated from the accelerometer measurements can be used in a first mode when the user's body orientation is known and a second mode when the user's orientation is assumed to be unknown. The first mode can be used, for example, when the user is standing upright, in which case the rotation angle is itself the orientation. A "locked" rotation angle can be estimated, for example, by taking an average of the calculated rotation angle values. For example, 10, 15, 20, or otherwise, calculated rotation angle values. In the second mode, the hardware controller can track a running window of a predetermined size (for example, 10, 15, 20, 25, 30, or otherwise), and estimate a running window average of the rotation angle values. If the estimated running window average vary by less than a specific angle (for example, 5, 10, 15, or otherwise), the window is considered to be stable. Within the stable window, if the normalized acceleration magnitude (which is the magnitude of the acceleration a divided by the magnitude of gravitation acceleration g) and its standard deviation each fall within allowed first and second margins respectively, the average of estimated rotational angle values of all the stable windows can be output as the wafer orientation. Optionally, the magnitude of the acceleration can be compared to the magnitude of gravitational acceleration prior to and/or after determining the wafer's orientation. If the magnitude of the acceleration is significantly different from the magnitude of gravitational acceleration (for example, by a certain percentage or otherwise), or has a high variance, the hardware controller can stop determining the wafer orientation or discard the calculated wafer orientation as being unreliable.

Figure 19:
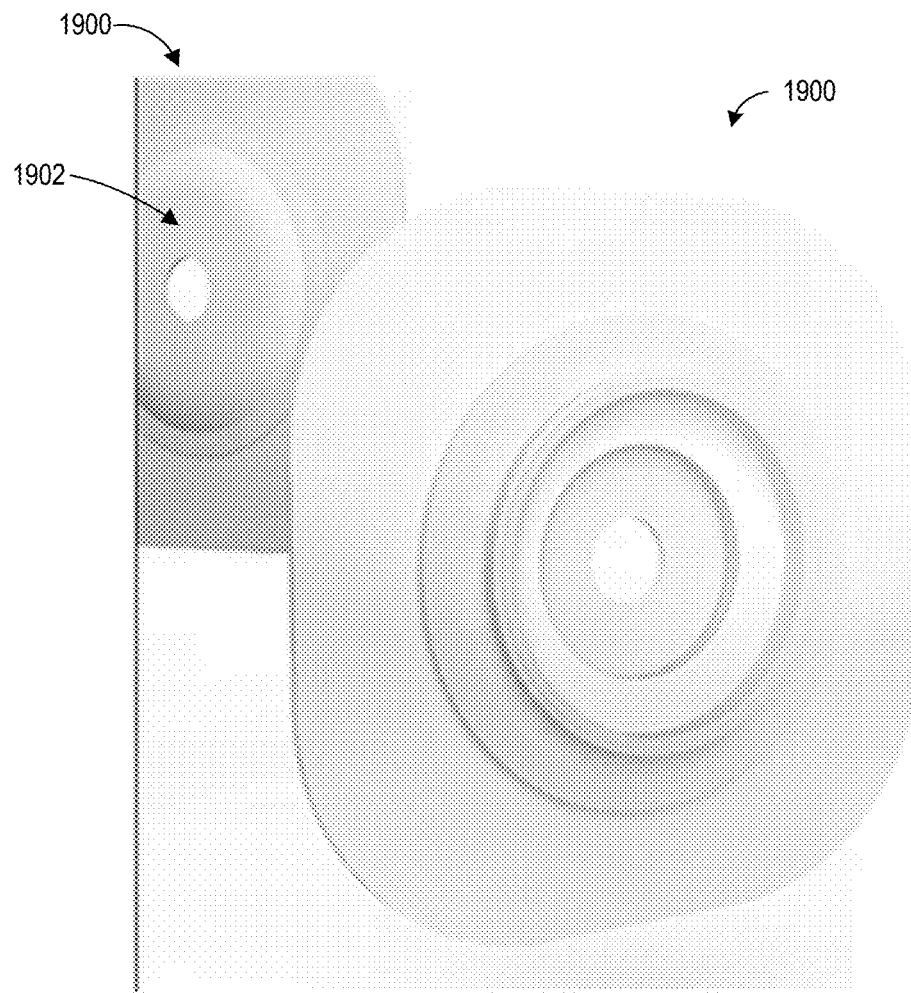
FIG. 19 illustrates an example convex wafer or baseplate.

The wafer in FIG. 19 is an example convex wafer 1900. The convex wafer 1900 can have any of the features of the wafer 200 disclosed herein. Unlike a generally flat wafer, the convex wafer 1900 has a protrusion or convex interface 1902 on the back, that is, the user-facing side to accommodate users with a recessed or retracted stoma. The convex interface 1902 can curve inward toward the stoma for better fit and reduced leak. The convex interface 1902 can be due to a convex portion 2208 on the wafer coupling component 204, such as shown in FIGS. 22A-22D. This convex design can allow for a softer, more flexible and/or conforming convex experience for certain users. The convex wafer may be used with any type of ostomy bags disclosed herein, such as the diagnostic bag, the analysis bag, and/or the maintenance bag. The convex wafer disclosed herein can include any of the sensors disclosed herein. The convex wafer can provide patients with convex needs access to all the same data and insights that is delivered through ostomy systems including a substantially flat wafer.

Any type of ostomy bags and/or wafers disclosed herein can optionally be waterproof so that they can be worn in the shower or while swimming. Such bags and/or wafers can include a variety of woven outer materials, including polyester, nylon, micro suede and/or a combination of any of these that would be coated in a water repellant coating or other suitable materials and/or coatings.

Terminology

Many other variations than those described herein will be apparent from this disclosure. For example, depending on the embodiment, certain acts, events, or functions of any of the algorithms described herein can be performed in a different sequence, can be added, merged, or left out altogether (for example, not all described acts or events are necessary for the practice of the algorithms). Moreover, in certain embodiments, acts or events can be performed concurrently, for example, through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a hardware processor comprising digital logic circuitry, a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, for example, a combination of a DSP and a microprocessor, a plurality of microprocessors, one or more microprocessors in conjunction with a DSP core, or any other such configuration. A computing environment can include any type of computer system, including, but not limited to, a computer system based on a microprocessor, a mainframe computer, a digital signal processor, a portable computing device, a device controller, or a computational engine within an appliance, to name a few.

The steps of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC.

Conditional language used herein, such as, among others, "can," "might," "may," "for example," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Disjunctive language such as the phrase "at least one of X, Y and Z," unless specifically stated otherwise, is to be understood with the context as used in general to convey that an item, term, etc. may be either X, Y, or Z, or a combination thereof. Thus, such conjunctive language is not generally intended to imply that certain embodiments require at least one of X, at least one of Y and at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others.

What is claimed is:

1. An ostomy wafer configured to couple an ostomy bag to a user, the wafer comprising:
   a sensor layer comprising a plurality of temperature sensors surrounding a stoma opening of the wafer, wherein the plurality of temperature sensors are configured to be separated into four quadrants; and
   a hardware processor, the hardware processor configured to detect inflammation or fever, or both based at least in part on signals from one or more of the plurality of temperature sensors, wherein the hardware processor is configured to determine an average temperature of the temperature sensors in a same quadrant.

2. The ostomy wafer of claim 1, wherein the hardware processor is further configured to calculate a difference between a short-term average temperature and a long-term average temperature of the temperature sensors in the same quadrant.

3. The ostomy wafer of claim 2, wherein the hardware processor is further configured to calculate a rate of change of a difference between the short-term and long-term average temperatures.

4. The ostomy wafer of claim 1, wherein the sensor layer comprises at least in part a ring-shaped main body and a plurality of fingers extending radially inwardly from the main body, the plurality of temperature sensors located on the plurality of fingers.

5. The ostomy wafer of claim 1, further comprising an accelerometer.

6. The ostomy wafer of claim 5, wherein the hardware processor is further configured to determine a location of inflammation based on at least one signal from at least one of the temperature sensors and data from the accelerometer.

7. The ostomy wafer of claim 1, wherein the hardware processor is configured to detect fever in response to detection of a temperature growth across all four quadrants.

* * * * *